（12） United States Patent
Lin

(10) Patent No.: US 11,180,858 B2
(45) Date of Patent: *Nov. 23, 2021

(54) GAS GENERATOR

(71) Applicant: Hsin-Yung Lin, Shanghai (CN)

(72) Inventor: Hsin-Yung Lin, Shanghai (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/573,947

(22) Filed: Sep. 17, 2019

(65) Prior Publication Data

US 2020/0010962 A1    Jan. 9, 2020

Related U.S. Application Data

(63) Continuation of application No. 14/875,629, filed on Oct. 5, 2015, now Pat. No. 10,465,300.

(30) Foreign Application Priority Data

Oct. 16, 2014 (TW) .................................. 103135889
Oct. 16, 2014 (TW) .................................. 103135890
(Continued)

(51) Int. Cl.
*C25B 1/04* (2021.01)
*C25B 15/02* (2021.01)
(Continued)

(52) U.S. Cl.
CPC ............. *C25B 1/04* (2013.01); *A61M 16/101* (2014.02); *A61M 16/107* (2014.02);
(Continued)

(58) Field of Classification Search
CPC ................. C25B 9/13; C25B 9/15; C25B 9/00
See application file for complete search history.

(56) References Cited

U.S. PATENT DOCUMENTS 4,014,777 A    3/1977  Brown
4,936,878 A    6/1990  Gustavsson et al.
(Continued)

FOREIGN PATENT DOCUMENTS

CA    2158068 A1    9/1994
CA    2906103 A1    9/2014
(Continued)

OTHER PUBLICATIONS

Office Action dated Apr. 24, 2019 for Australian Application 2018202304.
(Continued)

*Primary Examiner* — Harry D Wilkins, III

(57) ABSTRACT

The present invention provides a gas generator, comprising a water tank and an electrolysis device. The water tank has a first hollow portion for containing electrolyzed water. The electrolysis device is disposed inside the first hollow portion of the water tank for electrolyzing the electrolyzed water to generate a hydrogen-oxygen mixed gas. When the electrolysis device starts to electrolyze the electrolyzed water, the first hollow portion of the water tank is filled with the electrolyzed water for standing at a full level of water. And after the electrolysis device electrolyzed the electrolyzed water, the level of water for the electrolyzed water filled into the first hollow portion of the water tank is higher than 95% of the full level of water. The gas generator of the present invention provides the design for saving space and nearly a zero gas chamber to reduce the possibility of explosions resulting from hydrogen-oxygen mixed gas.

18 Claims, 30 Drawing Sheets

(30) Foreign Application Priority Data

Oct. 16, 2014 (TW) .................. 103135891
Oct. 16, 2014 (TW) .................. 103135892
Oct. 16, 2014 (TW) .................. 103218377

(51) Int. Cl.
*C25B 15/08* (2006.01)
*A61M 16/14* (2006.01)
*A61M 16/10* (2006.01)
*C02F 1/461* (2006.01)
*A61M 15/08* (2006.01)
*A61M 11/06* (2006.01)
*C02F 103/02* (2006.01)
*C02F 1/00* (2006.01)
*C02F 1/36* (2006.01)

(52) U.S. Cl.
CPC ........... *A61M 16/14* (2013.01); *C02F 1/4618* (2013.01); *C25B 15/02* (2013.01); *C25B 15/08* (2013.01); *A61M 11/06* (2013.01); *A61M 15/08* (2013.01); *A61M 2202/0208* (2013.01); *C02F 1/008* (2013.01); *C02F 1/36* (2013.01); *C02F 2001/46152* (2013.01); *C02F 2103/026* (2013.01); *C02F 2201/46155* (2013.01); *C02F 2209/005* (2013.01); *C02F 2209/02* (2013.01); *C02F 2209/38* (2013.01); *C02F 2209/40* (2013.01); *C02F 2209/42* (2013.01); *C02F 2303/16* (2013.01); *Y02E 60/32* (2013.01); *Y02E 60/36* (2013.01)

(56) References Cited

U.S. PATENT DOCUMENTS

| | | | |
|---|---|---|---|
| 5,520,858 A | 5/1996 | Yamaguchi et al. | |
| 6,202,991 B1 | 3/2001 | Coniglio et al. | |
| 6,527,940 B1* | 3/2003 | Shimamune | C02F 1/4618 |
| | | | 205/464 |
| 6,740,436 B2* | 5/2004 | Chou | H01M 8/0656 |
| | | | 429/413 |
| 7,258,779 B2 | 8/2007 | Casey et al. | |
| 7,318,885 B2 | 1/2008 | Omasa | |
| 2001/0009223 A1 | 7/2001 | Lee et al. | |
| 2008/0202921 A1 | 8/2008 | Wilkinson et al. | |
| 2009/0166191 A1 | 7/2009 | Sato et al. | |
| 2010/0025234 A1 | 2/2010 | Boo-Sung | |
| 2010/0206646 A1 | 8/2010 | Lin | |
| 2010/0236921 A1 | 9/2010 | Binglin | |
| 2011/0132750 A1 | 6/2011 | Talarico | |
| 2012/0279871 A1 | 11/2012 | Gotheil-Yelle | |
| 2013/0206586 A1 | 8/2013 | Lin | |
| 2013/0247905 A1 | 9/2013 | Miller et al. | |
| 2013/0255670 A1* | 10/2013 | Ott | A61M 16/16 |
| | | | 128/200.14 |
| 2015/0101926 A1* | 4/2015 | Burns | C25B 9/06 |
| | | | 204/277 |
| 2015/0144482 A1 | 5/2015 | Lin | |
| 2015/0144483 A1 | 5/2015 | Lin | |
| 2015/0159284 A1* | 6/2015 | Packer | C25B 9/08 |
| | | | 204/274 |
| 2015/0190604 A1 | 7/2015 | Lin | |
| 2015/0211131 A1* | 7/2015 | Jacobs | C25B 1/06 |
| | | | 204/236 |

FOREIGN PATENT DOCUMENTS

| | | |
|---|---|---|
| CA | 2854390 A1 | 12/2014 |
| CA | 2848440 A1 | 10/2015 |
| CN | 2127940 Y | 3/1993 |
| CN | 2594654 Y | 12/2003 |
| CN | 201064606 Y | 5/2008 |
| CN | 201147555 Y | 11/2008 |
| CN | 201285132 Y | 8/2009 |
| CN | 101843945 A | 9/2010 |
| CN | 101956205 A | 1/2011 |
| CN | 202430295 U | 9/2012 |
| CN | 202576577 U | 12/2012 |
| CN | 202898558 U | 4/2013 |
| CN | 203043245 U | 7/2013 |
| CN | 203291354 U | 11/2013 |
| CN | 203389458 U | 1/2014 |
| CN | 103785091 A | 5/2014 |
| CN | 103789784 A | 5/2014 |
| CN | 103789788 A | 5/2014 |
| CN | 103800979 A | 5/2014 |
| CN | 103806013 A | 5/2014 |
| CN | 203609733 U | 5/2014 |
| CN | 203613266 U | 5/2014 |
| CN | 203613267 U | 5/2014 |
| CN | 203683675 U | 7/2014 |
| DE | 102011119745 A1 | 6/2013 |
| DE | 202014004509 U1 | 8/2014 |
| DE | 202014004744 U1 | 8/2014 |
| EP | 2184382 A1 | 5/2010 |
| EP | 2589425 A1 | 5/2013 |
| JP | 06-128780 A | 5/1994 |
| JP | 2002129369 A | 5/2002 |
| JP | 2002155387 A | 5/2002 |
| JP | 2003105577 A | 4/2003 |
| JP | 2003105578 A | 4/2003 |
| JP | 2004131787 A | 4/2004 |
| JP | 2005054266 A | 3/2005 |
| JP | 2005240152 A | 9/2005 |
| JP | 2006022378 A | 1/2006 |
| JP | 2006043610 A | 2/2006 |
| JP | 2006057141 A | 3/2006 |
| JP | 2006131942 A | 5/2006 |
| JP | 2009275948 A | 11/2009 |
| JP | 2011099165 A | 5/2011 |
| JP | 2011168862 A | 9/2011 |
| JP | 3192728 U | 8/2014 |
| KR | 20020032272 A | 5/2002 |
| KR | 20090039685 A | 4/2009 |
| KR | 101076630 B1 | 10/2011 |
| KR | 20130136910 A | 12/2013 |
| RU | 2235151 C2 | 8/2004 |
| RU | 2011135150 A | 2/2013 |
| WO | WO2001049351 A2 | 7/2001 |
| WO | WO2013052957 A1 | 4/2013 |

OTHER PUBLICATIONS

Office Action dated Apr. 23, 2019 for Canadian Application 2964996.
Office Action dated Apr. 23, 2019 for Canadian Application 2965038.
Office Action dated Jul. 30, 2019 for Singapore Application 10201810540U.
Office Action dated Apr. 30, 2018 for Japanese Application No. 2017180654.
Office Action dated May 5, 2017 for Chinese Application No. 201410618949.8.
Office Action dated Jul. 4, 2017 for Chinese Application No. 201410620118.4.
Office Action dated Aug. 17, 2018 for Canadian Application No. 2,964,996.
Notification of Reason for Refusal dated Dec. 8, 2020 for related JP Patent Application No. 2019-087994.

* cited by examiner

GAS GENERATOR

CROSS-REFERENCE TO RELATED APPLICATIONS

This application is a continuation of U.S. application Ser. No. 14/875,629, filed Oct. 5, 2015 which claims the priority benefit of Taiwan Application Serial Nos. 103218377, 103135891, 103135892, 103135889, and 103135890, filed Oct. 16, 2014, the disclosure of which is incorporated herein by reference.

BACKGROUND OF THE INVENTION

1. Field of the Invention

The present invention relates to a gas generator, and more particularly, the present invention relates to a gas generator which can prevent explosions and has function of controlling the temperature of the electrolyzed water and cooling down the electrolyzed water after generated hydrogen-oxygen mixed gas.

2. Description of the Prior Art

People are always paying a great deal of attention on health developments. Many developments in medical technology are often targeted on treating diseases and prolonging human life. However, most of the treatments in the past are passive, which means that they only treat the disease when the disease occurs. These methods include operation, medication, radiation therapy, chronic diseases care, rehabilitation, corrective therapy, or even medical treatments for cancers. But in recent years, much of the research from medical experts are gradually moving towards preventive medical methods, such as research on healthy food, screening and preventing inherited diseases, which actively prevents diseases from occurring in the future. Because of the focus on prolonging human life, many anti-aging and anti-oxidation technologies including skin care products and anti-oxidation food/medicine are gradually being developed and have become increasingly popular to the general public.

Studies have found that there are instable oxygen species (O+), also known as free radicals, in the human body. The free radicals are usually generated due to diseases, diet, environment and one's lifestyle, but can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are also clinical experiments showing that patients who need to inhale a high concentration of oxygen for an extended period of time would experience lung damage and the lung damage, and they could be ameliorated by inhaling hydrogen.

In addition to healthy uses, the application of hydrogen-oxygen gas also can create hydrogen-oxygen fire to heat or burn, or clean up the carbon accumulated in engine as well.

Generally, hydrogen-oxygen gas is generated through electrolyzing liquid water. However, it's easy to generate high temperature in the electrolyzing process, which will allow the efficiency of electrolyzing to be decreased and cause energy consumption problems. Furthermore, to avoid hydrogen explosions, air-cooling type hydrogen-oxygen electrolysis tank are usually used, which is utilizing fan to cool down. However, if the fan malfunctions, the temperature of the electrolysis tank will be raised, and it's easy to cause hydrogen explosions.

SUMMARY OF THE INVENTION

Therefore, an aspect of the present invention is to provide a gas generator, which electrolyzes liquid water and generates hydrogen-oxygen mixed gas. Meanwhile, the gas generator of the present invention can maintain the quantity of the hydrogen-oxygen mixed gas in the water tank, and cool down the temperature of the hydrogen-oxygen mixed gas as well, to avoid gas explosions.

The present invention provides a gas generator, comprising a water tank and an electrolysis device. The water tank has a first hollow portion for containing electrolyzed water. The electrolysis device is disposed inside the first hollow portion of the water tank for electrolyzing the electrolyzed water to generate a hydrogen-oxygen mixed gas. When the electrolysis device starts to electrolyze the electrolyzed water, the first hollow portion of the water tank and the electrolysis device are filled with the electrolyzed water for standing at a full level of water. And after the electrolysis device electrolyzed the electrolyzed water, the level of water for the electrolyzed water filled into the first hollow portion of the water tank and the electrolysis device are higher than 90% of the full level of water.

After the electrolysis device electrolyzed the electrolyzed water, the electrolyzed water is filled into the first hollow portion of the water tank and the electrolysis device for allowing the level of water thereof to be between 90% of the full level of water and 99.99% of the full level of water.

The water tank can further comprise a pipe for outputting the hydrogen-oxygen mixed gas. When the electrolysis device pauses to electrolyze the electrolyzed water for generating the hydrogen-oxygen mixed gas, the pipe can be used to recharge the electrolyzed water for allowing the first hollow portion of the water tank and the electrolysis device to be filled with the electrolyzed water.

Additionally, the gas generator of the present invention can selectively further comprise a water pump, connected with the first hollow portion of the water tank for enforcing to circulate the electrolyzed water in the first hollow portion of the water tank and the electrolysis device.

The electrolysis device can further selectively comprise a partition and an electrolysis tank. The partition comprises a connecting hole. The partition is used to divide the first hollow portion into an upper portion and a lower portion. And the upper portion and the lower portion are connected through the connecting hole.

The electrolysis device can further selectively comprise a plurality of electrodes and a pad. The plurality of the electrodes is respectively disposed on the space inside the electrolysis tank for forming a plurality of electrode channels. The pad is disposed on the upper surface of each electrode and has a plurality of upper vias. The upper portion of the first hollow portion is connected with the plurality of electrode channels through the plurality of upper vias of the pad. And each electrode channel is respectively connected with the upper portion of the first hollow portion through the corresponding upper via.

The electrolysis tank can further selectively have a lower surface. The lower surface of the electrolysis tank has a plurality of lower vias. The lower portion of the first hollow portion is connected with the plurality of electrode channels through the plurality of lower vias of the lower surface of the electrolysis tank. And each electrode channel is respectively connected with the lower portion of the first hollow portion through the corresponding lower via.

The gas generator of the present invention can selectively further comprise a flow quantity detector. The flow quantity detector is coupled to the electrolysis device for detecting the flow quantity of the hydrogen-oxygen mixed gas, and further controlling the quantity of the hydrogen-oxygen mixed gas outputted from the electrolysis device. The flow quantity detector can selectively cut off the electrical connection between the electrolysis device and the power source. By means of the electrolyzed water is filled in the first hollow portion of the water tank and the electrolysis device, the present invention can maintain the quantity of the hydrogen-oxygen mixed gas in the water tank, and cool down the temperature of the hydrogen-oxygen mixed gas as well, to avoid gas explosions.

The gas generator of the present invention can selectively further comprise a power source. The plurality of electrodes comprise a negative plate, a positive plate, and a plurality of bipolar plates. The plurality of bipolar plates are disposed with space between the negative plate and the positive plate. The negative plate is connected to the negative pole of the power source. And the positive plate is connected to the positive pole of the power source.

The gas generator of the present invention can selectively further comprise a nebulized gas mixing tank. The nebulized gas mixing tank is connected to the water tank for receiving the hydrogen-oxygen mixed gas. The nebulized gas mixing tank generates a nebulized gas to be mixed with the hydrogen-oxygen mixed gas to form a healthy gas for user to breathe, wherein the nebulized gas is selected from a group consisting of water vapor, nebulized medicinal liquid, evaporated essential oil, and the combination thereof.

To summarize the statement mentioned above, the priority of the present invention is to provide a gas generator, comprising a water tank and an electrolysis device. The design for the electrolysis device disposed inside the water tank of the present invention can save space. Meanwhile, by means of the electrolyzed water filled in the first hollow portion of the water tank and the electrolysis device, the present invention can prevent chambers from existing in the water tank, and decrease the temperature of the electrolysis device to avoid gas explosions. Furthermore, the design for the gas outlet and the inlet opening of the electrolysis device of the present invention allows the electrolyzed water in the water tank to be recharged in the electrolysis device. The hydrogen-oxygen mixed gas generated by the electrolysis device can be outputted to the water tank to achieve the goal of gas-water circulation. Additionally, in the present invention, the design for the connection structure of the water pump, the water tank, and the electrolysis device can allow the electrolyzed water contained in the first hollow portion and the electrolysis device to be enforced to circulate, which allows the chamber in the water tank to be nearly zero so as to avoid gas explosions.

Furthermore, another aspect of the present invention is to provide a gas generator, which has the functions of controlling the temperature of the electrolyzed water and cooling down the electrolyzed water after generated hydrogen-oxygen mixed gas, which then allows the temperature of the electrolyzed water to be in a temperature range providing optimal electrolytic efficiency for effectively electrolyzing electrolyzed water to generate hydrogen-oxygen mixed gas, to solve the energy consumption problems.

The present invention provides a gas generator, comprising an electrolysis device, a cooling device, and a water pump. The electrolysis device contains electrolyzed water. The electrolysis device is used to electrolyze the electrolyzed water to generate a hydrogen-oxygen mixed gas. The cooling device is connected to the electrolysis device, used to cool down the electrolyzed water after the hydrogen-oxygen mixed gas is generated. And the water pump is connected between the cooling device and the electrolysis device, used to enforce to circulate the electrolyzed water.

Additionally, the gas generator of the present invention can selectively further comprise a microcomputer controller. The microcomputer controller is coupled to the water pump, used to detect the temperature of the electrolyzed water and control an inputting flow rate and an outputting flow rate of the water pump according to the detected temperature of the electrolyzed water.

The microcomputer controller can selectively comprise a temperature sensor. The temperature sensor is used to detect the temperature of the electrolyzed water.

The cooling device can selectively comprise a radiator and a fan. The radiator comprises a box and a radiating tube. The radiating tube is disposed in the box. And the fan is fixed on an outer surface of the box of the radiator.

Additionally, the gas generator of the present invention can selectively further comprise a water tank. The water tank has a first hollow portion. The first hollow portion of the water tank contains the electrolyzed water. The electrolysis device is disposed inside the first hollow portion of the water tank, wherein the first hollow portion is connected with the electrolysis device, the radiator is connected to the water tank, and the water pump is connected between the radiator and the water tank.

The water tank can selectively comprise an outlet opening and an inlet opening. The radiator can selectively comprise an inlet and an outlet. The inlet and the outlet of the radiator are connected through the radiating tube. The water pump can selectively comprise an inlet pipe and an outlet pipe. The outlet opening of the water tank is connected with the inlet of the radiator. The outlet of the radiator is connected with the inlet pipe of the water pump. And the outlet pipe of the water pump is connected with the inlet opening of the water tank.

Additionally, the gas generator of the present invention can selectively further comprise a nebulized gas mixing tank, wherein the nebulized gas mixing tank is coupled to the electrolysis device for receiving the hydrogen-oxygen mixed gas. The nebulized gas mixing tank generates a nebulized gas to be mixed with the hydrogen-oxygen mixed gas to form a healthy gas for user to breathe, wherein the nebulized gas is selected from a group consisting of water vapor, nebulized medicinal liquid, evaporated essential oil, and the combination thereof.

To summarize the statement mentioned above, the priority of the present invention is to provide a gas generator, comprising electrolysis device, cooling device, and water pump. The gas generator of the present invention can cool down the electrolyzed water after the hydrogen-oxygen mixed gas is generated through the cooling device, and enforce to circulate the electrolyzed water through the water pump to achieve the goal of heat radiation. Meanwhile, the present invention can allow the temperature of the electrolyzed water to be in a temperature range providing optimal electrolytic efficiency for effectively electrolyzing electrolyzed water to generate hydrogen-oxygen mixed gas, to solve the energy consumption problems.

Furthermore, another aspect of the present invention is to provide a gas generator, comprising electrolysis device, cooling device, and water pump. The electrolysis device contains electrolyzed water. The electrolysis device is used to electrolyze the electrolyzed water to generate a hydrogen-oxygen mixed gas. The cooling device is connected to the electrolysis device, used to cool down the electrolyzed water after the hydrogen-oxygen mixed gas is generated. And the water pump is connected between the cooling device and the electrolysis device, used to enforce to circulate the electrolyzed water. Wherein, the temperature of the electrolyzed water contained in the electrolysis device is a normal electrolyzed temperature, and the normal electrolyzed temperature is between 55° C. to 65° C.

Additionally, the gas generator of the present invention can selectively further comprise a microcomputer controller. The microcomputer controller is coupled to the water pump, used to detect the temperature of the electrolyzed water and control an inputting flow rate and an outputting flow rate of the water pump according to the detected temperature of the electrolyzed water.

The cooling device can selectively comprise a radiator and a fan. The radiator comprises a box and a radiating tube. The radiating tube is disposed in the box. And the fan is fixed on an outer surface of the box of the radiator.

Additionally, the gas generator of the present invention can selectively further comprise a water tank. The water tank has a first hollow portion. The first hollow portion of the water tank contains the electrolyzed water. The electrolysis device is disposed inside the first hollow portion of the water tank, wherein the first hollow portion is connected with the electrolysis device, the radiator is connected to the water tank, and the water pump is connected between the radiator and the water tank.

Additionally, the gas generator of the present invention can selectively further comprise a nebulized gas mixing tank, wherein the nebulized gas mixing tank is coupled to the electrolysis device for receiving the hydrogen-oxygen mixed gas. The nebulized gas mixing tank generates a nebulized gas to be mixed with the hydrogen-oxygen mixed gas to form a healthy gas for user to breathe, wherein the nebulized gas is selected from a group consisting of water vapor, nebulized medicinal liquid, evaporated essential oil, and the combination thereof.

To summarize the statement mentioned above, the priority of the present invention is to provide a gas generator, comprising electrolysis device, cooling device, and water pump. Wherein, the temperature of the electrolyzed water contained in the electrolysis device is between 55° C. to 65° C. The gas generator of the present invention can cool down the electrolyzed water after the hydrogen-oxygen mixed gas is generated through the cooling device, and enforce to circulate the electrolyzed water through the water pump to achieve the goal of heat radiation. Meanwhile, the present invention can allow the temperature of the electrolyzed water to be in a temperature range (55° C. to 65° C.) providing optimal electrolytic efficiency for effectively electrolyzing electrolyzed water to generate hydrogen-oxygen mixed gas, to solve the energy consumption problems.

Furthermore, another aspect of the present invention is to provide a gas generator, comprising an electrolysis device and a condense filter. The condense filter is connected to the electrolysis device for condensing the hydrogen-oxygen mixed gas and filtering the impurities of the hydrogen-oxygen mixed gas. When the electrolysis device is paused to electrolyze the electrolyzed water for generating the hydrogen-oxygen mixed gas, the gas outlet via of the condense filter can be used to input recharged water, and the impurities can be flushed back to the electrolysis device and the first hollow portion via the recharged water through the gas inlet via and the pipe.

To summarize the statement mentioned above, the priority of the present invention is to provide a gas generator, comprising electrolysis device and condense filter. In the present invention, the hydrogen-oxygen mixed gas generated by the electrolysis device can be cooled down and filtered by the condense filter, to provide a hydrogen-oxygen mixed gas which is appropriate for human to breathe. Meanwhile, through the design of the present invention, the electrolyte can be flushed back to the electrolysis device when recharging water, used to decrease the consumption of the electrolyte and avoid the electrolyte to block the condense filter.

Furthermore, another aspect of the present invention is to provide a gas generator, comprising an electrolysis device and a humidification device. The humidification device comprises a hollow body, a second pipe, at least one outputting pipe, and an oscillation device. The hollow body is used to contain recharged water. The second pipe is disposed on the hollow body and connected to the electrolysis device for receiving the hydrogen-oxygen mixed gas. The at least one outputting pipe is disposed in the hollow body and connected to the second pipe. The surface of the at least one outputting pipe has a plurality of vias. The oscillation device is disposed in the hollow body and positioned under the at least one outputting pipe for oscillating the recharged water. When the electrolysis device is electrolyzing the electrolyzed water to generate the hydrogen-oxygen mixed gas, the hydrogen-oxygen mixed gas is outputted through the plurality of vias of the at least one outputting pipe, and then the hydrogen-oxygen mixed gas is humidified by the recharged water which is oscillated by the oscillation device.

Additionally, the hydrogen-oxygen mixed gas outputted through the plurality of vias of the at least one outputting pipe can be combined with the recharged water which is oscillated by the oscillation device to generate hydrogen water.

Additionally, the gas generator of the present invention can further comprise a hand-held atomize device for receiving the humidified hydrogen-oxygen mixed gas. The hand-held atomize device can generate a nebulized gas to be mixed with the humidified hydrogen-oxygen mixed gas to form a healthy gas for a user to breathe.

To summarize the statement mentioned above, the priority of the present invention is to provide a gas generator, comprising electrolysis device and humidification device. In the present invention, the hydrogen-oxygen mixed gas generated by the electrolysis device can be humidified by the humidification device, to provide a hydrogen-oxygen mixed gas which is appropriate for human to breathe. Additionally, through the humidification device, the hydrogen-oxygen mixed gas generated by the electrolysis device can generate hydrogen water with higher concentration of hydrogen-oxygen mixed gas. In practical application, the concentration of hydrogen-oxygen mixed gas of the hydrogen water can be adjusted according to the requirement of the user. Furthermore, the design of the present invention can be used to recharge recharged water. Meanwhile, the electrolyte will be flushed back to the electrolysis device to recover the filter ability of the circulating channel, avoid the circulating channel to be blocked or corroded, and decrease the consumption of the electrolyte.

Furthermore, another aspect of the present invention is to provide a gas generator, comprising a hydrogen water generator. The hydrogen water generator comprises a container, a gas inlet pipe, a thinning pipe, an oscillation device, and a liquid inputting/outputting structure. The surface of the thinning pipe having a plurality of vias for allowing the gas comprising hydrogen to be formed as a plurality of thin bubbles after outputting from the thinning pipe to the water through the vias. The oscillation device can be used to oscillate the water contained in the container for mixing the thin bubbles with water to form hydrogen water and humidified gas.

The advantages and spirits of the invention may be understood by the following recitations together with the appended drawings.

BRIEF DESCRIPTION OF THE APPENDED DRAWINGS

Some of the embodiments will be described in detail, with reference to the following figures, wherein like designations denote like members, wherein.

The advantages, spirits, and features of the present invention will be explained and discussed with embodiments and figures as following.

DETAILED DESCRIPTION OF THE INVENTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1A:
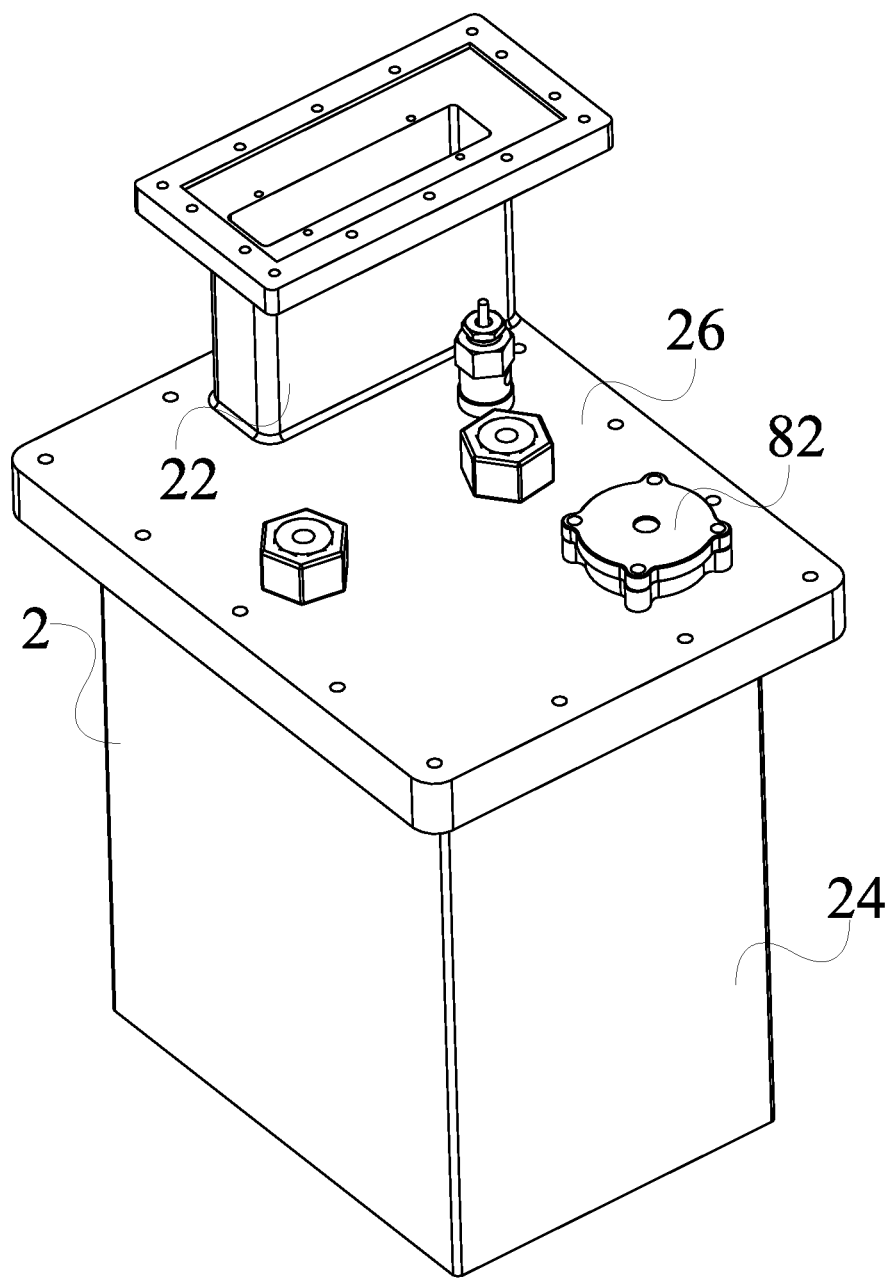
FIG. 1A and FIG. 1B show a schematic diagram of the gas generator in the first embodiment with different visual angle of the present invention.
Figure 1B:
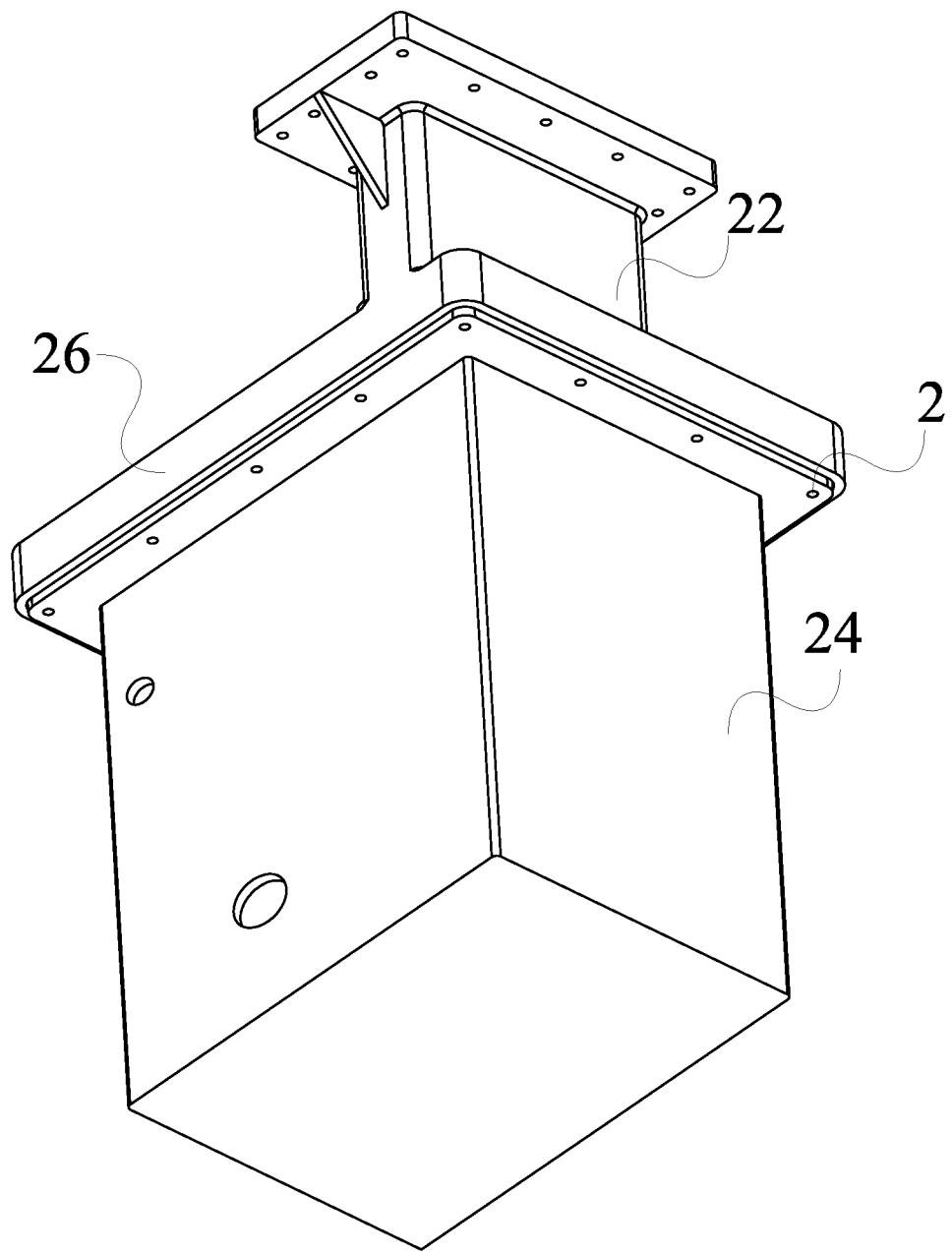
Figure 2A:
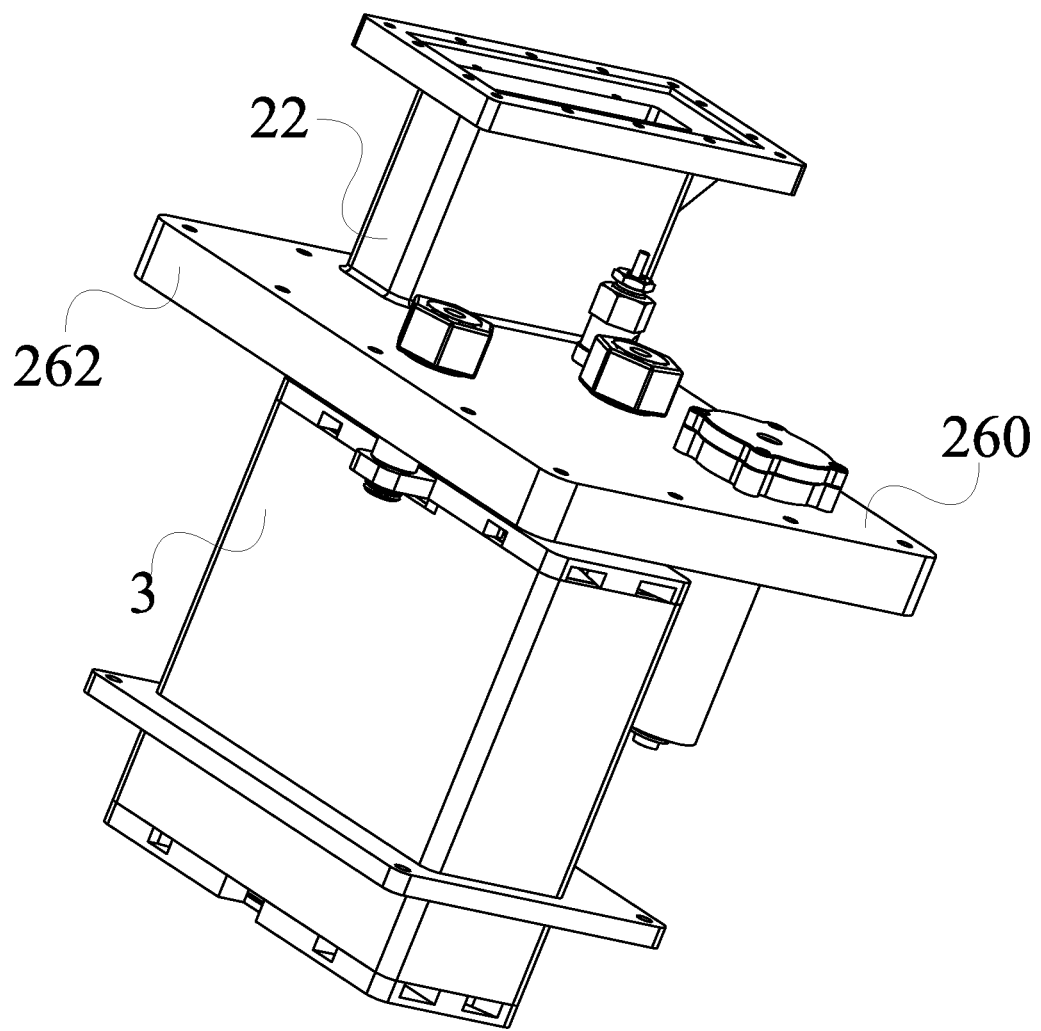
FIG. 2A and FIG. 2B show a schematic diagram with different visual angles of the present invention which only has the combination of the upper cover of the water tank and the electrolysis device in the embodiment shown in FIG. 1A.
Figure 2B:
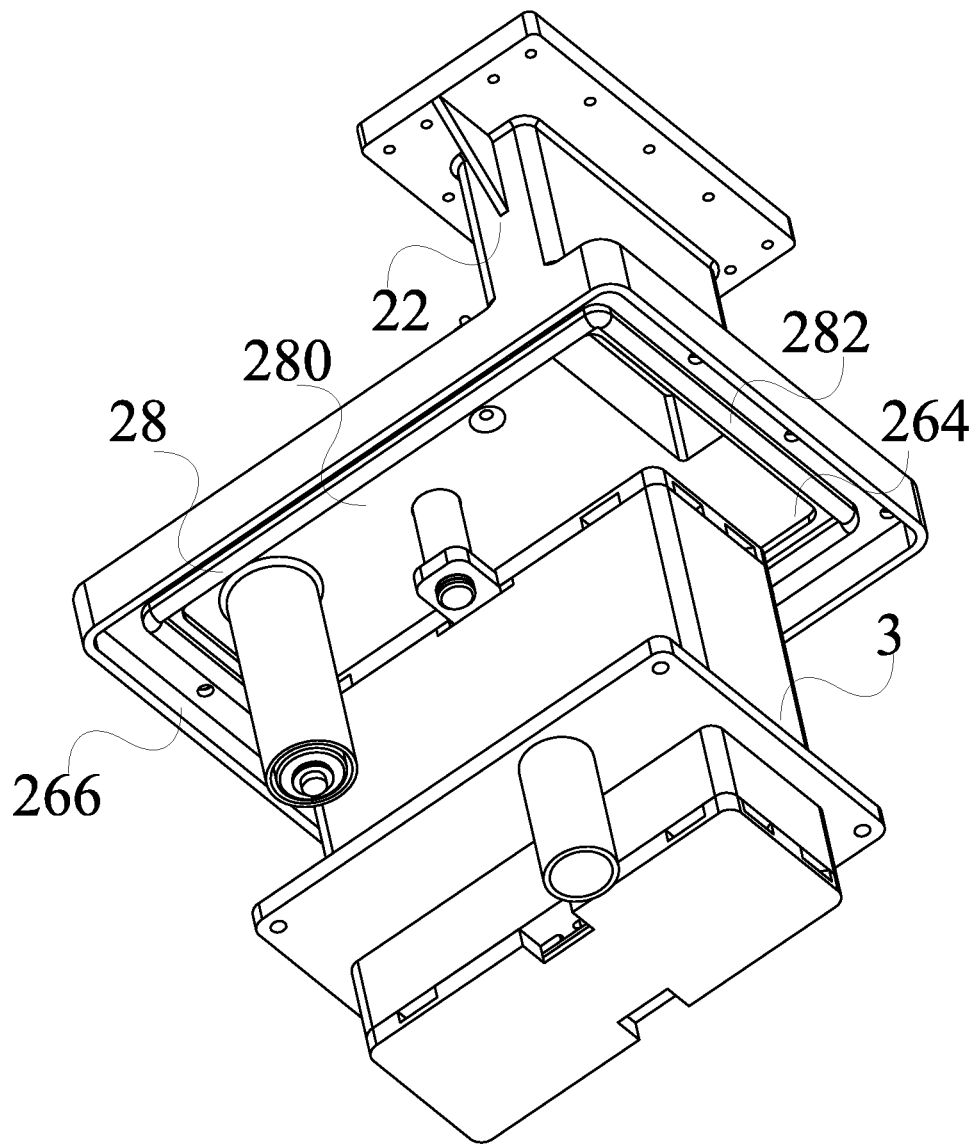

The present invention provides a gas generator. The gas generator is an explosion-proof gas generator. Please refer to FIG. 1A, FIG. 1B, FIG. 2A, and FIG. 2B. FIG. 1A and FIG. 1B show a schematic diagram of the gas generator in the first embodiment with different visual angles of the present invention, FIG. 2A and FIG. 2B show a schematic diagram with different visual angles of the present invention which only has the combination of the upper cover of the water tank and the electrolysis device in the embodiment shown in FIG. 1A. As shown in figures, in the first embodiment, the gas generator 1 of the present invention comprises a water tank 2 and an electrolysis device 3. The water tank 2 contains an electrolyzed water W. The electrolysis device 3 is disposed inside the water tank 2 for electrolyzing the electrolyzed water W to generate a hydrogen-oxygen mixed gas G. When the electrolysis device 3 starts to electrolyze the electrolyzed water W, the water tank 2 and the electrolysis device 3 are filled with the electrolyzed water W for standing at a full level of water. And after the electrolysis device 3 electrolyzed the electrolyzed water W, the level of water for the electrolyzed water W filled into the water tank 2 and the electrolysis device 3 is higher than 90% of the full level of water. The following statement will explain the design of each element of the present invention respectively.

The water tank 2 of the present invention has a first hollow portion 20 and a pipe 22. The first hollow portion 20 of the water tank 2 is used to contain an electrolyzed water W. The major constituent of the electrolyzed water W is pure water. According to the requirement, a few electrolytes can be added into the pure water, such as sodium hydroxide, calcium carbonate, and sodium chloride. The pipe 22 of the water tank 2 is connected with the first hollow portion 20 of the water tank 2, used to output the hydrogen-oxygen mixed gas G generated from the electrolysis device 3 and recharge the electrolyzed water W in the water tank 2.

Figure 3A:
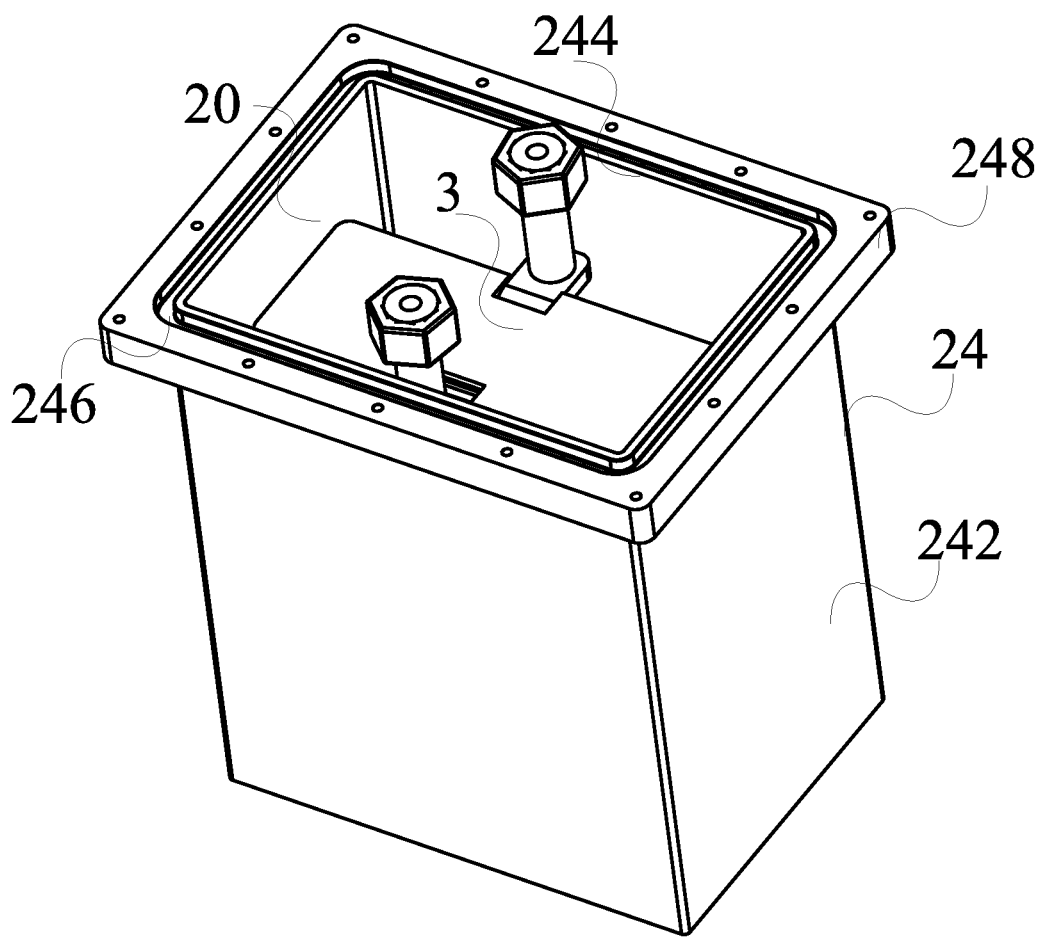
FIG. 3A and FIG. 3B show a schematic diagram with different visual angles of the present invention which only has the combination of the electrolysis device and the tank body of the water tank in the embodiment shown in FIG. 1A.
Figure 3B:
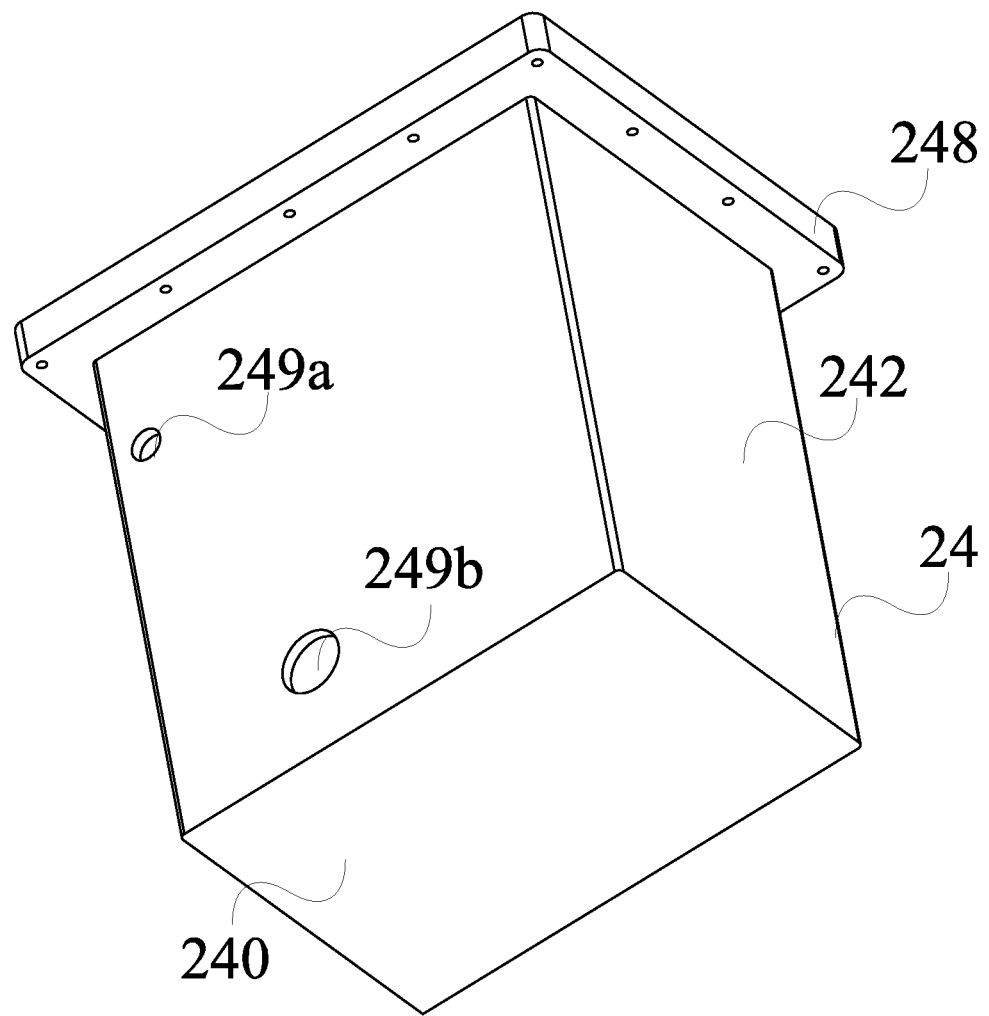

Additionally, please refer to FIG. 3A and FIG. 3B. FIG. 3A and FIG. 3B show a schematic diagram with different visual angles of the present invention which only has the combination of the electrolysis device and the tank body of the water tank in the embodiment shown in FIG. 1A. In this embodiment, the water tank 2 further comprises a tank body 24 and a cover body 26.

The tank body 24 of the water tank 2 can be approximately divided into a first base 240 and a first wall portion 242. The first wall portion 242 is formed by extending outward from the inner surface of the first base 240 along the direction of the normal vector of the inner surface. The first wall portion 242 encloses the first hollow portion 20. The other end of the first hollow portion 20 relative to the first base 240 has a first opening portion 244. Meanwhile, the other side of the first wall portion 242 relative to the first base 240 has a first side margin 248. And the first side margin 248 encloses the first opening portion 244 mentioned above. Additionally, the tank body 24 of the water tank 2 further comprises an outlet opening 249a and an inlet opening 249b. In this embodiment, the outlet opening 249a of the tank body 24 of the water tank 2 is connected with the two surfaces of the first wall portion 242 of the tank body 24 of the water tank 2 relative to the direction of the electrolysis device 3, and the inlet opening 249b of the tank body 24 of the water tank 2 is connected with the two surfaces of the first wall portion 242 of the tank body 24 of the water tank 2 relative to the direction of the electrolysis device 3. The outlet opening 249a and the inlet opening 249b of the tank body 24 of the water tank 2 is connected with each other through the first hollow portion 20. The outlet opening 249a and the inlet opening 249b of the tank body 24 of the water tank 2 can be used to connect a water pump and the first hollow portion 20 of the water tank 2.

Figure 10A:
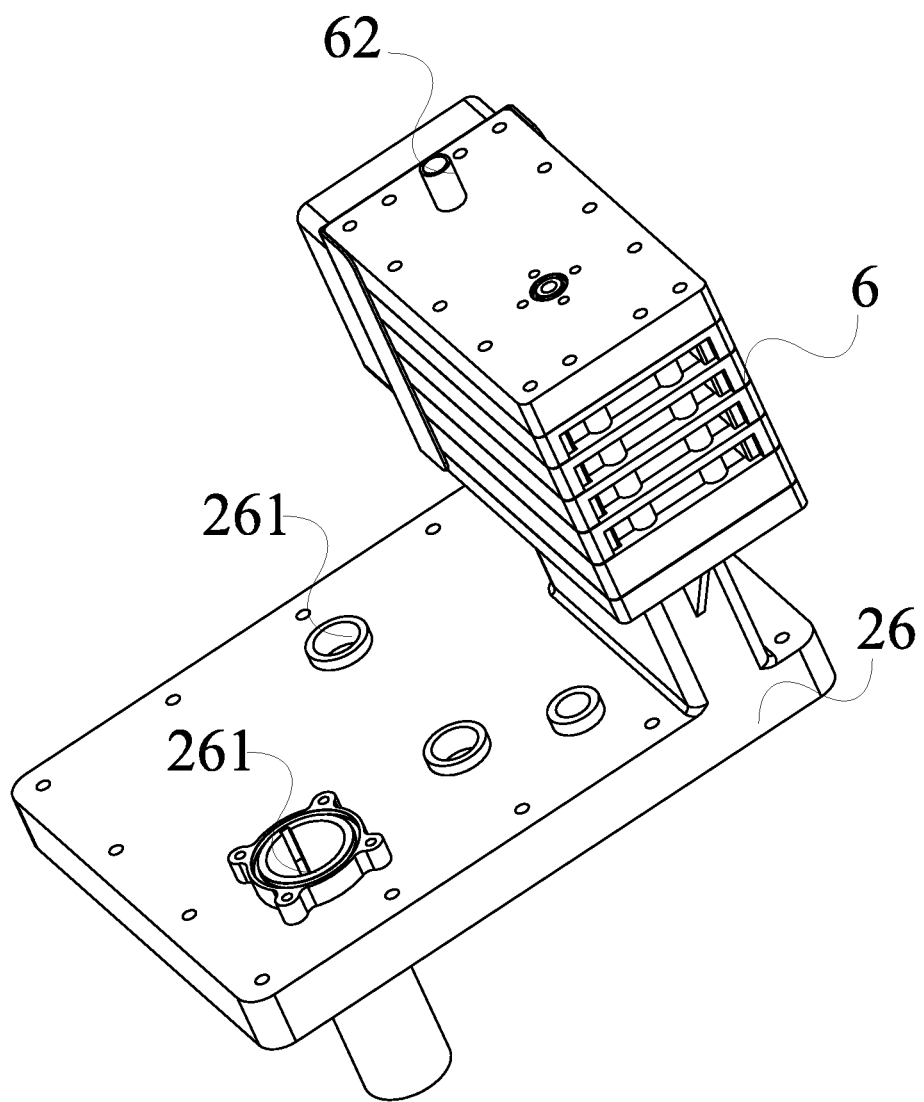
FIG. 10A and FIG. 10B show a schematic diagram with different visual angles of the present invention which only has the combination of the condense filter and the cover body of the water tank in the embodiment shown in FIG. 9A.
Figure 10B:
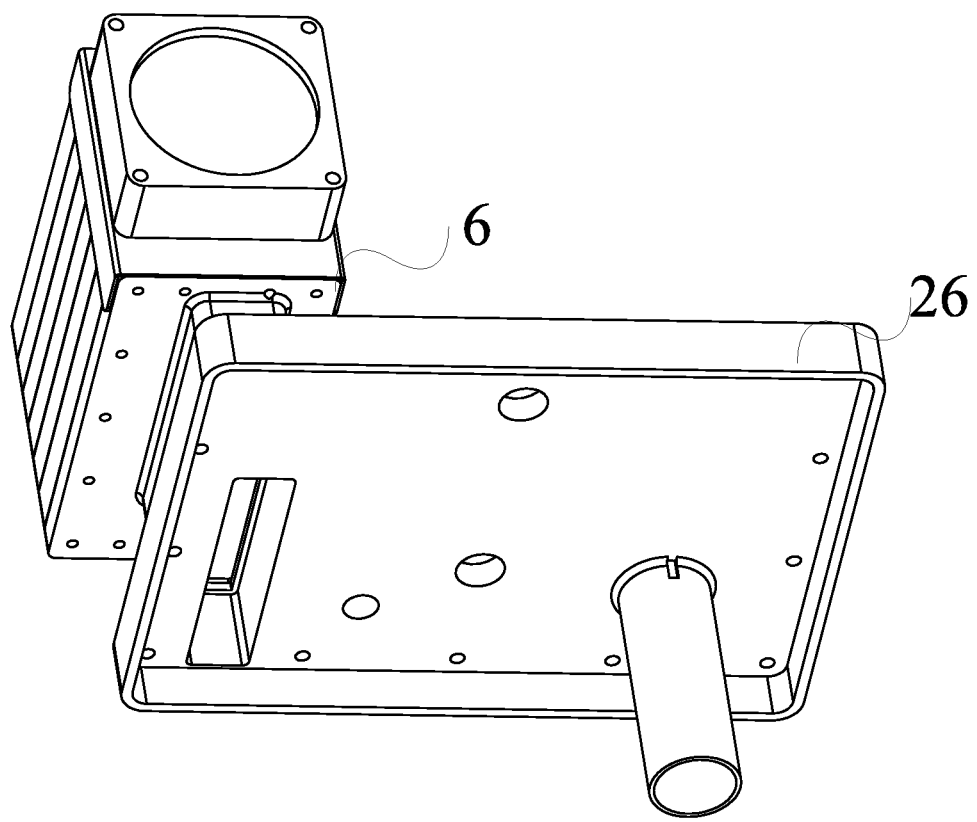
Figure 11:
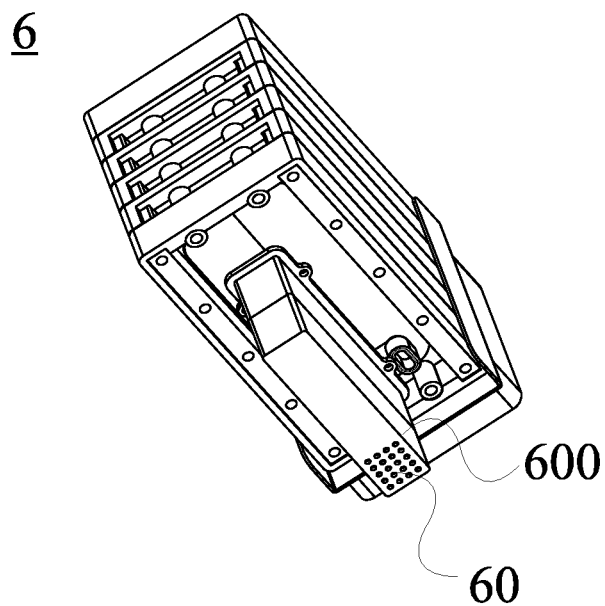
FIG. 11 shows a schematic diagram of the present invention in the embodiment shown in FIG. 10A without the cover body of the water tank.
Figure 12:
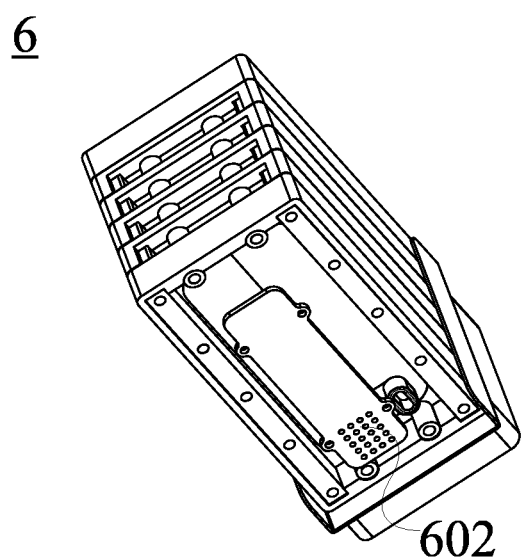
FIG. 12 shows a schematic diagram of the present invention in the embodiment shown in FIG. 11 without the filter gauze.
Figure 13:
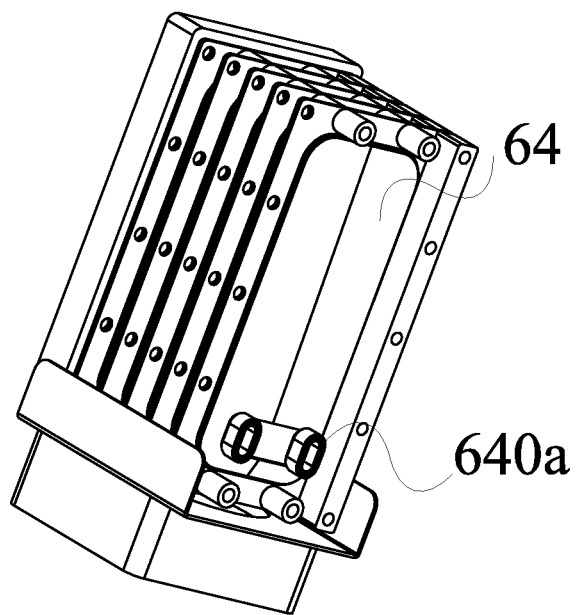
FIG. 13 shows a schematic diagram of the present invention in the embodiment shown in FIG. 12 without the cover of the filter gauze.
Figure 14A:
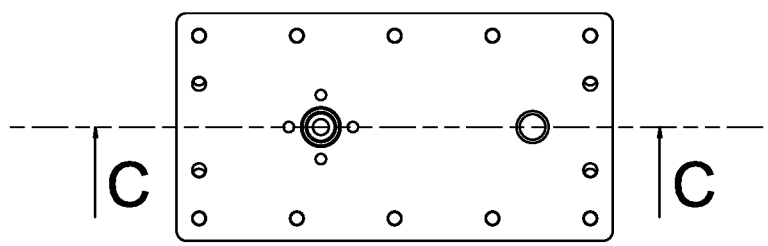
FIG. 14A and FIG. 14B show a top view diagram and a cross-section diagram crossing along the C-C line of the top view diagram of the condense filter of the gas generator in the embodiment shown in FIG. 10A of the present invention.
Figure 14B:
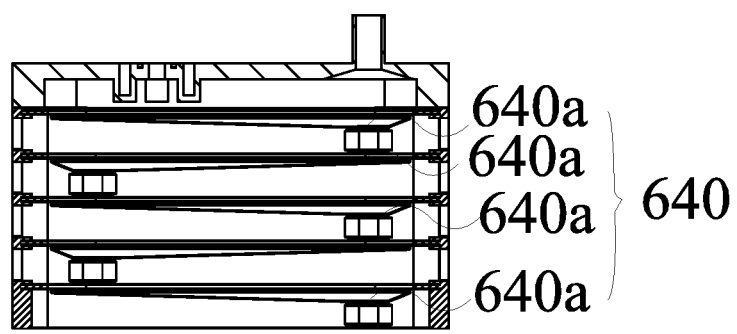

The cover body 26 of the water tank 2 can be approximately divided into a second base 260 and a second wall portion 262. The second wall portion 262 is formed by extending outward from the inner surface of the second base 260 along the direction of the normal vector of the inner surface. The second wall portion 262 encloses a second hollow portion 264. The other end of the second hollow portion 264 relative to the second base 260 has a second opening portion 266. The cover body 26 of the water tank 2 can dispose the first side margin 248 of the tank body 24 of the water tank 2 in the second hollow portion 264 through the second opening portion 266. Pipe 22 can be disposed on the second base 260 of the cover body 26 of the water tank 2, and connect the two surfaces of the second base 260 of the cover body 26 of the water tank 2 relative to the direction of the tank body 24 of the water tank 2. However, the present invention is not limited to the statement mentioned above. In practical application, pipe 22 also can be replaced by a pilot hole or other elements which has the function of output/input. The cover body 26 of the water tank 2 further comprises a plurality of cover holes (as shown in FIG. 10A). The plurality of cover holes connect the two surfaces of the second base 260 of the cover body 26 of the water tank 2 relative to the direction of the tank body 24 of the water tank 2, used for the electrode column of the electrolysis device 3 to pass through and then be disposed on the electrolysis device 3, or used for the detector (such as flow quantity detector, water level meter, safety valve) to pass through and then be disposed on the cover body 26 of the water tank 2.

Additionally, in this embodiment, the water tank 2 further comprises a seal 28, disposed between the tank body 24 and the cover body 26 of the water tank 2, used to allow the tank body 24 and the cover body 26 of the water tank 2 to be combined tightly. The seal 28 has a third opening portion 280. When the seal 28 is disposed between the tank body 24 and the cover body 26 of the water tank 2, the third opening portion 280 of the seal 28 encloses a plurality of cover holes 261 and the second opening portion 266. The corresponding surface of the tank body 24 of the water tank 2 and the seal 28 can further have a first embed structure 246 and a corresponding third embed structure 282 respectively. The first embed structure 246 and the corresponding third embed structure 282 can be embedded with each other. The first embed structure 246 encloses the first opening portion 244. The third embed structure 282 encloses the third opening portion 280.

Figure 4A:
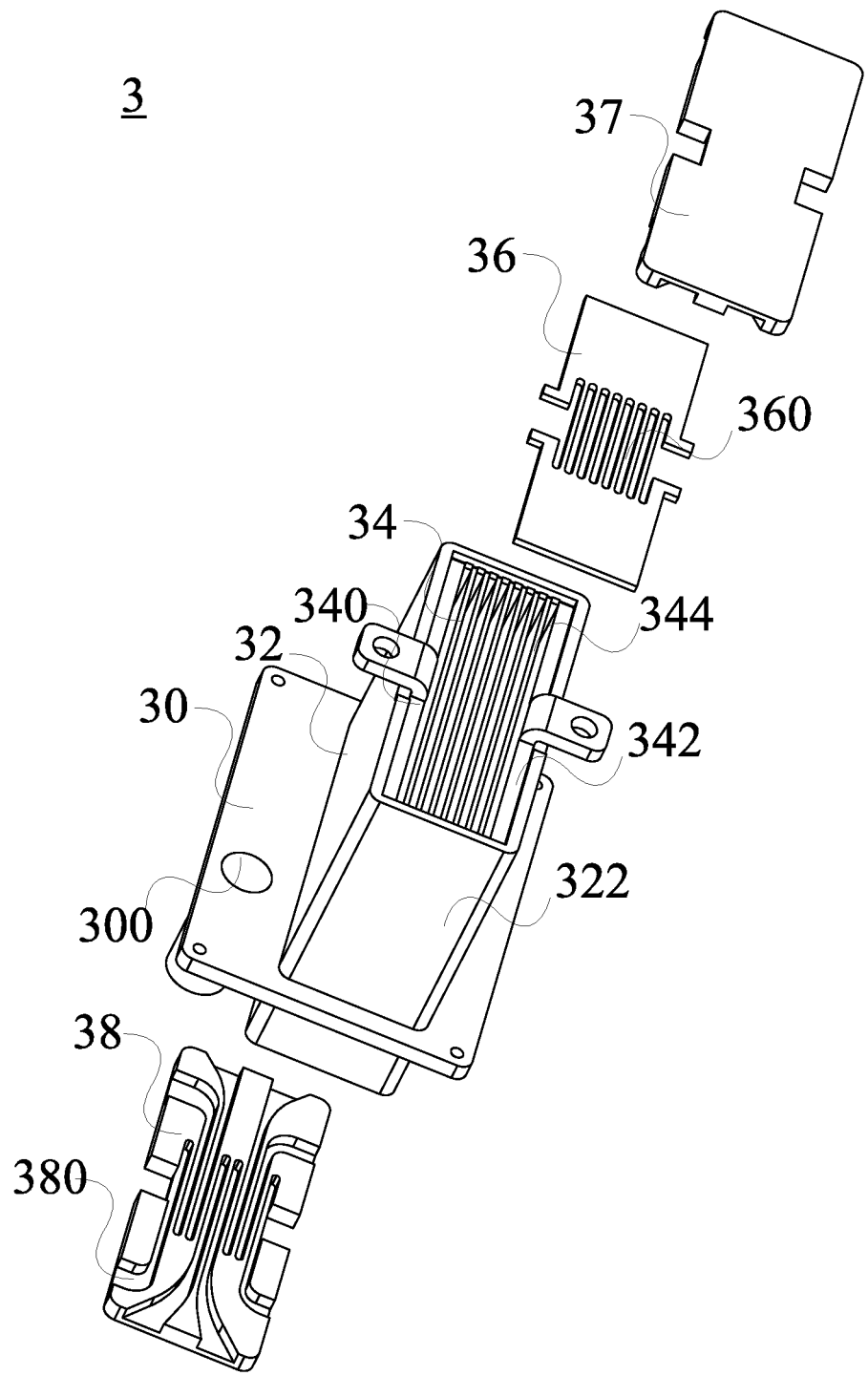
FIG. 4A and FIG. 4B show an explosion diagram of the electrolysis device of the gas generator with different visual angles in the embodiment shown in FIG. 1A of the present invention.
Figure 4B:
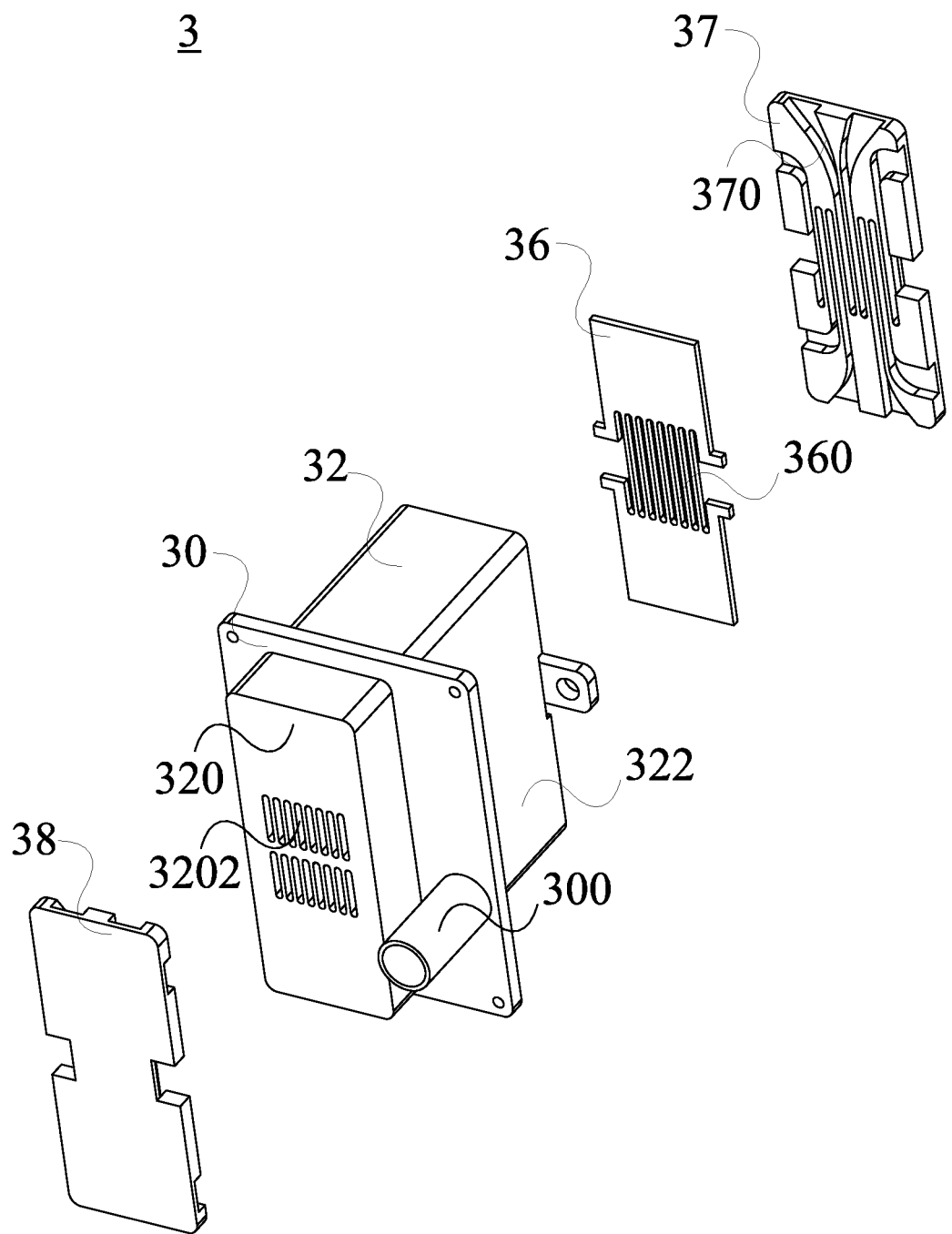

Please refer to FIG. 4A and FIG. 4B. FIG. 4A and FIG. 4B show an explosion diagram of the electrolysis device of the gas generator with different visual angles in the embodiment shown in FIG. 1A of the present invention. The electrolysis device 3 comprises an electrolysis tank 32, a plurality of electrodes 34, a pad 36, an upper cover body 37, and a lower cover body 38. The plurality of electrodes 34 are respectively disposed on the space inside the electrolysis tank 32 and formed a plurality of electrode channels S1. The pad 36 is disposed on the upper surface of each electrode 34. The upper cover body 37 is covered on the other end of the pad 36 relative to the electrolysis tank 32. The lower cover body 38 is covered on the other end of the lower surface of the electrolysis tank 32 relative to the upper cover body 37.

Figure 5A:
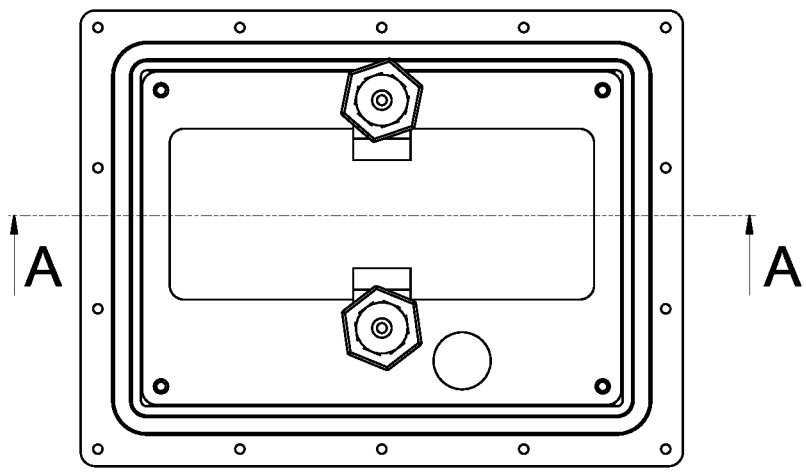
FIG. 5A and FIG. 5B show a top view diagram and a cross-section diagram crossing along the A-A line of the top view diagram of the tank body of the water tank and the electrolysis device of the gas generator in the embodiment shown in FIG. 3A of the present invention.
Figure 5B:
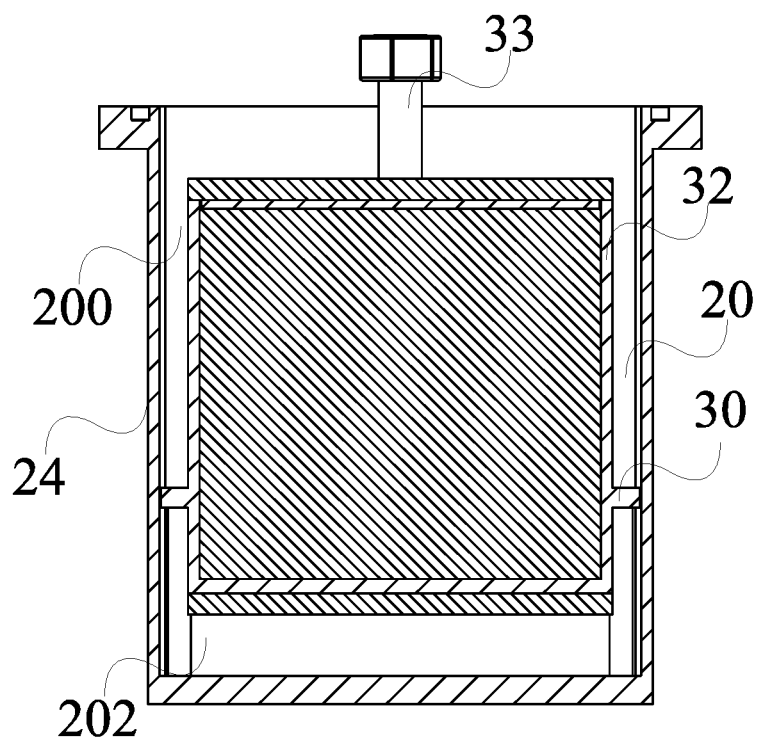

Please refer to FIG. 5A and FIG. 5B. FIG. 5A and FIG. 5B show a top view diagram and a cross-section diagram crossing along the A-A line of the top view diagram of the tank body of the water tank and the electrolysis device of the gas generator in the embodiment shown in FIG. 3A of the present invention. The electrolysis device further has a partition 30. The partition 30 is formed by extending outward from the side surface of the electrolysis tank relative to the water tank 2 along the direction of the normal vector of the side surface, used to divide the first hollow portion 20 of the water tank 2 into an upper portion 200 and a lower portion 202. The partition 30 comprises a connecting hole 300. The connecting hole 300 connects the two surfaces of the partition 30 relative to the direction of the first base 240 of the tank body 24 of the water tank 2. The upper portion 200 and the lower portion 202 of the first hollow portion 20 are connected through the connecting hole. The design of the connecting hole is not limited to this embodiment. In practical application, the amount and the shape of the connecting hole can be selected or designed according to the practical requirement.

Figure 6:
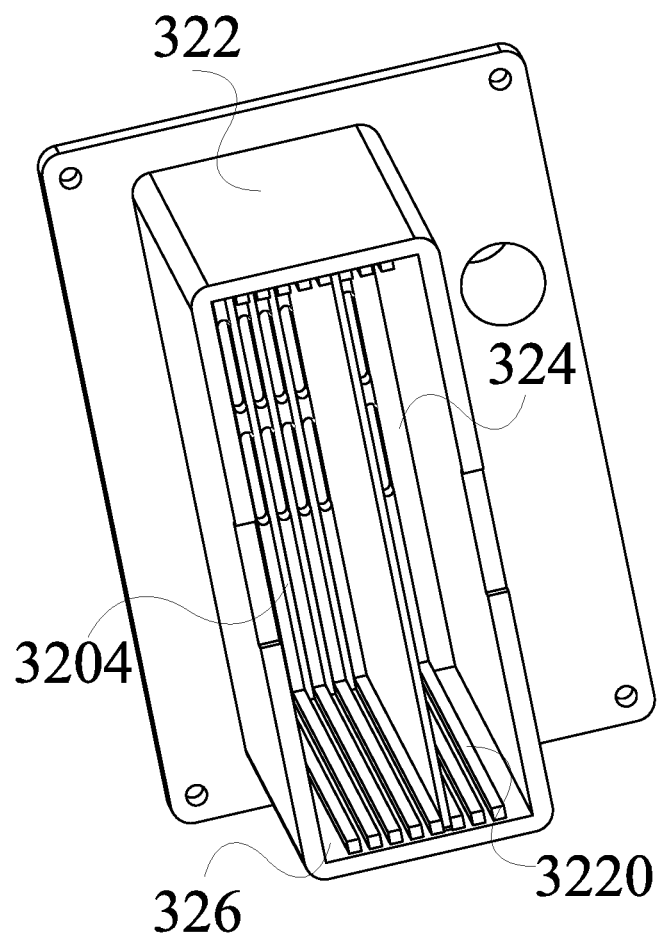
FIG. 6 shows a schematic diagram with different visual angles of the present invention which only has the combination of the electrolysis tank, the partition, and the electrodes in the embodiment shown in FIG. 1A.

Please refer to FIG. 6. FIG. 6 shows a schematic diagram with different visual angles of the present invention which only has the combination of the electrolysis tank, the partition, and the electrodes in the embodiment shown in FIG.

1A. The electrolysis tank 32 can be approximately divided into a fourth base 320 and a fourth wall portion 322. The fourth wall portion 322 is formed by extending outward from the inner surface of the fourth base 320 along the direction of the normal vector of the inner surface. The fourth wall portion 322 encloses the fourth hollow portion 324. The other end of the fourth hollow portion 324 relative to the fourth base 320 has a fourth opening portion 326. The fourth hollow portion 324 is adapted to contain the electrolyzed water W. Additionally, in order to explain the design of the electrolysis tank of the present invention, FIG. 6 omits a plurality of electrodes of the present invention. However, in practical application, the design thereof can be selected according to the practical requirement.

Figure 7A:
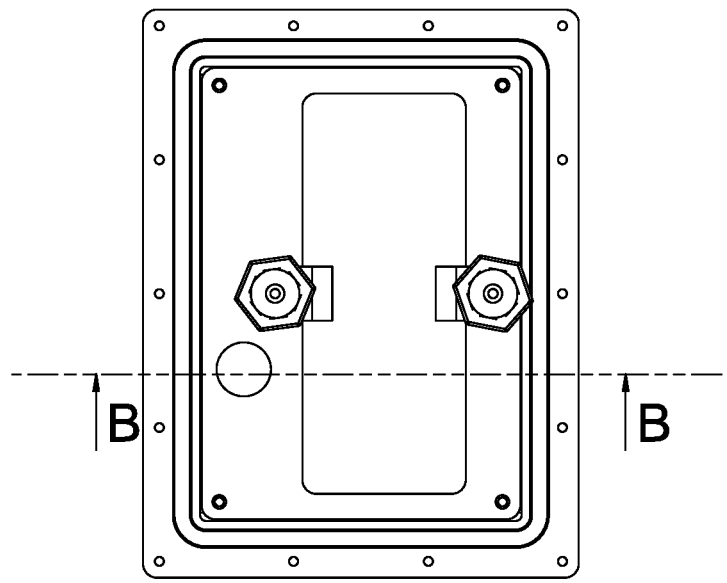
FIG. 7A and FIG. 7B show a top view diagram and a cross-section diagram crossing along the B-B line of the top view diagram of the tank body of the water tank and the electrolysis device of the gas generator in the embodiment shown in FIG. 3A of the present invention.
Figure 7B:
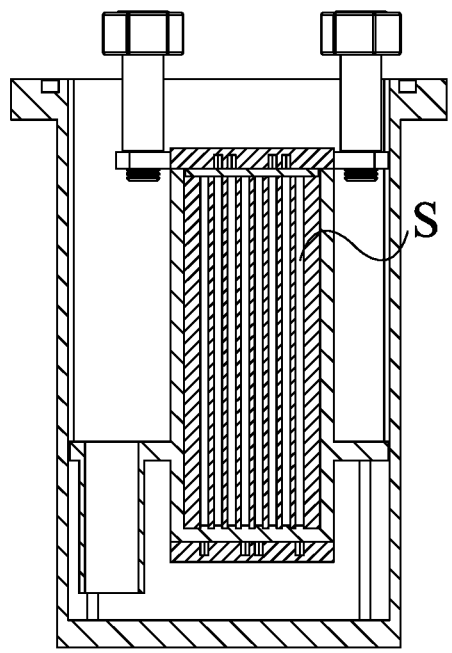

Please refer to FIG. 5A, FIG. 5B, FIG. 6, FIG. 7A, and FIG. 7B. FIG. 7A and FIG. 7B show a top view diagram and a cross-section diagram crossing along the B-B line of the top view diagram of the tank body of the water tank and the electrolysis device of the gas generator in the embodiment shown in FIG. 3A of the present invention. In this embodiment, the lower surface of the electrolysis tank 32 is the fourth base 320 of the electrolysis tank 32. The fourth base 320 of the electrolysis tank 32 has a plurality of lower vias 3202. The plurality of lower vias 3202 connect the two surfaces of the fourth base 320 of the electrolysis tank 32 relative to the direction of the first base 240 of the tank body 24 of the water tank 24. The fourth base 320 of the electrolysis tank 32 further has a plurality of fillisters 3204. The plurality of fillisters 3204 are formed by extending inward from the surface of the fourth base 320 of the electrolysis tank 32 relative to the fourth opening portion 326 along the direction of the normal vector of the surface. Each fillister 3204 is separately disposed between the lower via 3202 and the adjacent lower via 3202. The plurality of fillisters 3204 can be used to dispose the electrodes 34. Meanwhile, the fourth wall portion 322 of the electrolysis tank 32 further has a plurality of fix columns 3220. The plurality of fix columns 3220 are formed by extending outward from the surface of the fourth wall portion 322 relative to the plurality of lower via 3202 along the direction of the normal vector of the surface. The fix column 3220 and the adjacent fix column 3220 can be used to fix the electrodes 34 disposed in the fillister 3204. When the plurality of electrodes 34 are respectively disposed on the space in the fillister 3204 of the electrolysis tank 32 and fixed between the fix column 3220 and the adjacent fix column 3220, a plurality of electrode channels S1 will be formed in the electrolysis tank 32. Each electrode channel S1 can be connected with the lower portion 202 of the first hollow portion 20 respectively through the corresponding lower via 3202.

Pad 36 has a plurality of upper vias 360. The plurality of the upper vias 360 connect the two surfaces of the pad 36 relative to the direction of the electrolysis tank 32. Additionally, each electrode channel S1 also can be connected with the upper portion 200 of the first hollow portion 20 respectively through the corresponding upper via 360.

The plurality of electrodes 34 comprise a negative plate 340, a positive plate 342, and a plurality of bipolar plates 344. The plurality of bipolar plates 344 are disposed on the space between the negative plate 340 and the positive plate 342. In this embodiment, the electrolysis device 3 further comprises two electrode columns 33, used to fix the negative plate 340 and the positive plate 342 on the cover body 26 of the water tank 2 respectively for disposing the electrolysis device 3 in the midair in the water tank 2. Additionally, in this embodiment, the gas generator further comprises a power source (not shown in the figure). The negative plate 340 can be connected to the negative pole of the power source, and the positive plate 342 can be connected to the positive pole of the power source.

The upper cover body 37 comprises at least a first channel 370. As shown in FIG. 4B, the first channel 370 is formed by extending inward from the surface of the upper cover body 37 relative to the pad 36 along the direction of the normal vector of the surface. The plurality of upper vias 360 on the pad 36 are connected with the first hollow portion 20 through the at least one first channel 370.

The lower cover body 38 comprises at least a second channel 380. As shown in FIG. 4A, the second channel 380 is formed by extending inward from the surface of the lower cover body 38 relative to the fourth base 320 of the electrolysis tank 32 along the direction of the normal vector of the surface. The plurality of lower vias 3202 on the fourth base 320 of the electrolysis tank 32 is connected with the first hollow portion 20 through the at least one second channel 380.

Figure 8:
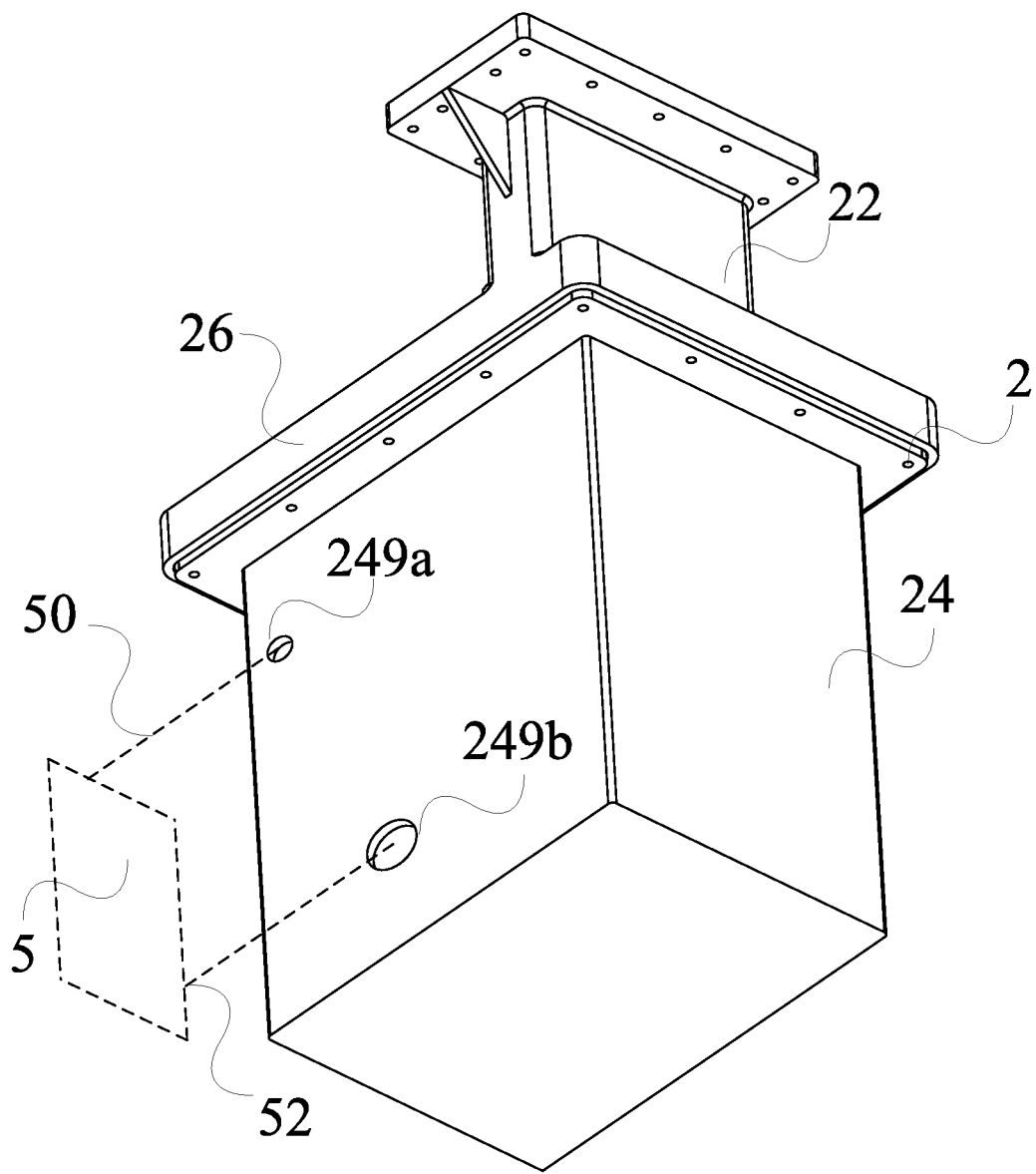
FIG. 8 shows a schematic diagram of the gas generator in the second embodiment of the present invention.

Additionally, please refer to FIG. 8. FIG. 8 shows a schematic diagram of the gas generator in the second embodiment of the present invention. In the second embodiment, the gas generator 1 of the present invention further comprises a water pump 5 (shown by dotted line only in FIG. 8). The water pump 5 can be used to enforce to circulate the electrolyzed water W contained in the first hollow portion 20 and the electrolysis device 3. The water pump 5 comprises an inlet pipe 50 and an outlet pipe 52. The outlet pipe 52 of the water pump 5 is used to connect the water pump 5 and the inlet opening 249b of the water tank 2. The inlet pipe 50 of the water pump 5 is used to connect the water pump 5 and the outlet opening 249a of the water tank 2.

Figure 15A:
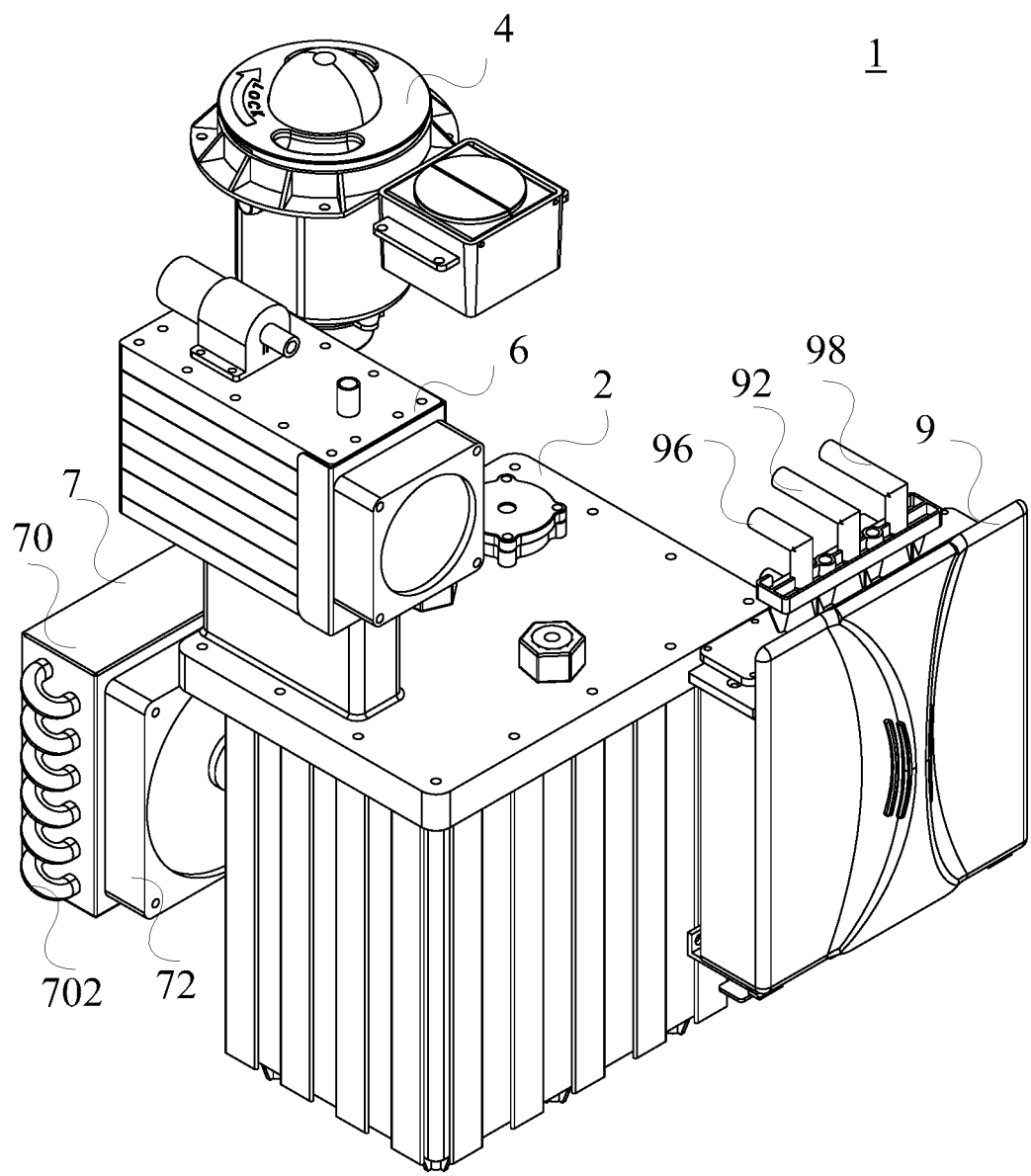
FIG. 15A and FIG. 15B show a schematic diagram of the gas generator in the fourteenth embodiment with different visual angle of the present invention.

Additionally, in the third embodiment, the gas generator 1 of the present invention further comprises a nebulized gas mixing tank 4 (as shown in FIG. 15A). The nebulized gas mixing tank 4 can be coupled to the electrolysis device 3 for receiving the hydrogen-oxygen mixed gas G. The nebulized gas mixing tank 4 can generate a nebulized gas G2 and be mixed with the hydrogen-oxygen mixed gas G to form a healthy gas for user to breathe. In practical application, the nebulized gas G2 can be selected from a group consisting of water vapor, nebulized medicinal liquid, evaporated essential oil, and the combination thereof.

After explaining the design of each element in the statement mentioned above, the following statement will describe the combination method and the application of each element of the gas generator of the present invention.

In the electrolysis device 3 which is assembled completely, plurality of electrodes is disposed with space in the electrolysis tank 32, the pad 36 is disposed on the upper surface of each electrode 34, the upper cover body 37 is covered on the other end of the pad 36 relative to the electrolysis tank 32, and the lower cover body 38 is covered on the other end of the lower surface of the electrolysis tank 32 relative to the upper cover body 37.

In the water tank 2 and the electrolysis device 3 which is assembled completely, the positive plate 342 and the negative plate 340 of the electrolysis device 3 are fixed on the cover body 26 of the water tank 2 respectively through two electrode columns 33. And the detector (such as flow quantity detector 82) are passed through the plurality of cover holes 261 of the cover body 26 of the water tank 2 and disposed on the cover body 26 of the water tank 2. The seal 28 is disposed on the tank body 24 of the water tank 2. The seal 28 and the tank body 24 of the water tank 2 are embedded with each other through the third embed structure 282 of the seal 28 and the first embed structure 246 of the tank body 24 of the water tank 2. The first side margin 248 of the tank body 24 of the water tank 2 is covered in the second hollow portion 264 of the cover body 26 of the water tank 2 through the second opening portion 266 of the cover body 26 of the water tank 2, for allowing the tank body 24 of the water tank 2 and the cover body 26 of the water tank 2 to be combined tightly, and allowing the electrolysis device 3 to be disposed in the midair in the water tank 2. Wherein, the first hollow portion 20 of the water tank 2 is connected with the electrolysis device 3.

In the water tank 2, the electrolysis device 3, and the water pump 5 which is assembled completely, the water tank 2 and the water pump 5 are connected with each other through the connection of the outlet pipe 52 of the water pump 5 and the inlet opening 249b of the water tank 2 and the connection of the inlet pipe 50 of the water pump 5 and the outlet opening 249a of the water tank 2. Additionally, in the third embodiment, the nebulized gas mixing tank 4 is connected to the electrolysis device 3.

In practical application, the water tank 2 contains electrolyzed water W, the electrolysis device 3 is disposed in the water tank 2 for electrolyzing the electrolyzed water W to generate a hydrogen-oxygen mixed gas G. The hydrogen-oxygen mixed gas G generated in the electrode channel S1 is outputted into the first hollow portion 20 through the corresponding upper via 360 of the pad 36 and the corresponding first channel 370 of the upper cover body 37. The hydrogen-oxygen mixed gas G inputted into the first hollow portion 20 is further outputted through the pipe 22 of the water tank 2 for the user to breathe. But the present invention is not limited to the statement mentioned above. In practical application, the hydrogen-oxygen mixed gas G inputted into the first hollow portion 20 can further be mixed with the nebulized gas G2 generated from the nebulized gas mixing tank 4 to form healthy gas for user to breathe.

Additionally, when the electrolysis device 3 pauses to electrolyze the electrolyzed water W for generating the hydrogen-oxygen mixed gas G, the pipe 22 can be used to recharge the electrolyzed water W for allowing the first hollow portion 20 and the electrolysis device 3 to be filled with the electrolyzed water W. The electrolyzed water W recharged in the first hollow portion 20 can be outputted to corresponding electrode channel S1 through the second channel 380 of the lower cover body 38 of the electrolysis device 3 and the plurality of lower via 3202, for providing the needed electrolyzed water W when the electrolysis device 3 is electrolyzing. Wherein, when the electrolysis device 3 starts to electrolyze the electrolyzed water W, the water tank 2 and the electrolysis device 3 are filled with the electrolyzed water W for standing at a full level of water. After the electrolysis device 3 electrolyzed the electrolyzed water W, the level of water for the electrolyzed water W filled into the water tank 2 and the electrolysis device 3 is still higher than 90% of the full level of water. In practical application, the gas generator of the present invention detects the level of water in the first hollow portion of the water tank and the electrolysis device through water level meter to control whether the electrolyzed water is needed to be recharged or not, which allows the level of water in the first hollow portion of the water tank and the electrolysis device to be between 90% of the full level of water and 99.99% of the full level of water. Therefore, the design of the gas generator of the present invention can prevent gas chambers from existing in the water tank, and further decrease the temperature of the electrolysis device, to reduce the possibility of gas explosions resulting from high temperature and enhance the safety thereof.

Additionally, the first hollow portion 20 of the water tank 2 is further connected with the water pump 5. The water pump 5 can be used to enforce to circulate the electrolyzed water W contained in the first hollow portion 20 and the electrolysis device 3. The electrolyzed water in the upper portion 200 and the lower portion 202 of the first hollow portion 20 is circulated through the connecting hole 300. Wherein, after the electrolysis device 3 electrolyzed the electrolyzed water W, the electrolyzed water w is filled into the first hollow portion 20 of the water tank 2 and the electrolysis device 3 for allowing the level of water thereof to be between 90% of the full level of water and 99.99% of the full level of water. Additionally, the gas generator of the present invention provides the design for nearly zero gas chamber through enforcing to circulate the electrolyzed water contained in the first hollow portion and the electrolysis device to control the pressure or storage quantity of the hydrogen-oxygen mixed gas in the water tank to reduce the possibility of gas explosions.

Additionally, the flow quantity detector 82 is coupled to the electrolysis device 3 to detect the flow quantity of the hydrogen-oxygen mixed gas G, and then controlling the outputted quantity of the hydrogen-oxygen mixed gas G from the electrolysis device 3 according to the detected flow quantity of the hydrogen-oxygen mixed gas G. Wherein, the flow quantity detector 82 can selectively cut the electrical connection between the electrolysis device 3 and the power source (not shown in the figure) off.

To summarize the statement mentioned above, the design of the present invention, which is disposing the electrolysis device in the water tank, can save place. Meanwhile, through the electrolyzed water filled in the first hollow portion of the water tank and the electrolysis device, the present invention can prevent gas chambers from existing in the water tank, and decrease the temperature of the electrolysis device, to avoid gas explosions. Furthermore, the design for the gas outlet and the inlet opening of the electrolysis device of the present invention allows the electrolyzed water in the water tank to be recharged into the electrolysis device. The hydrogen-oxygen mixed gas generated by the electrolysis device can be outputted to the water tank to achieve the goal of gas-water circulation. Additionally, in the present invention, the design for the connection structure of the water pump, the water tank, and the electrolysis device can allow the electrolyzed water contained in the first hollow portion and the electrolysis device to be enforced to circulate, which allows the chamber in the water tank to be nearly zero to avoid gas explosions.

Figure 17:
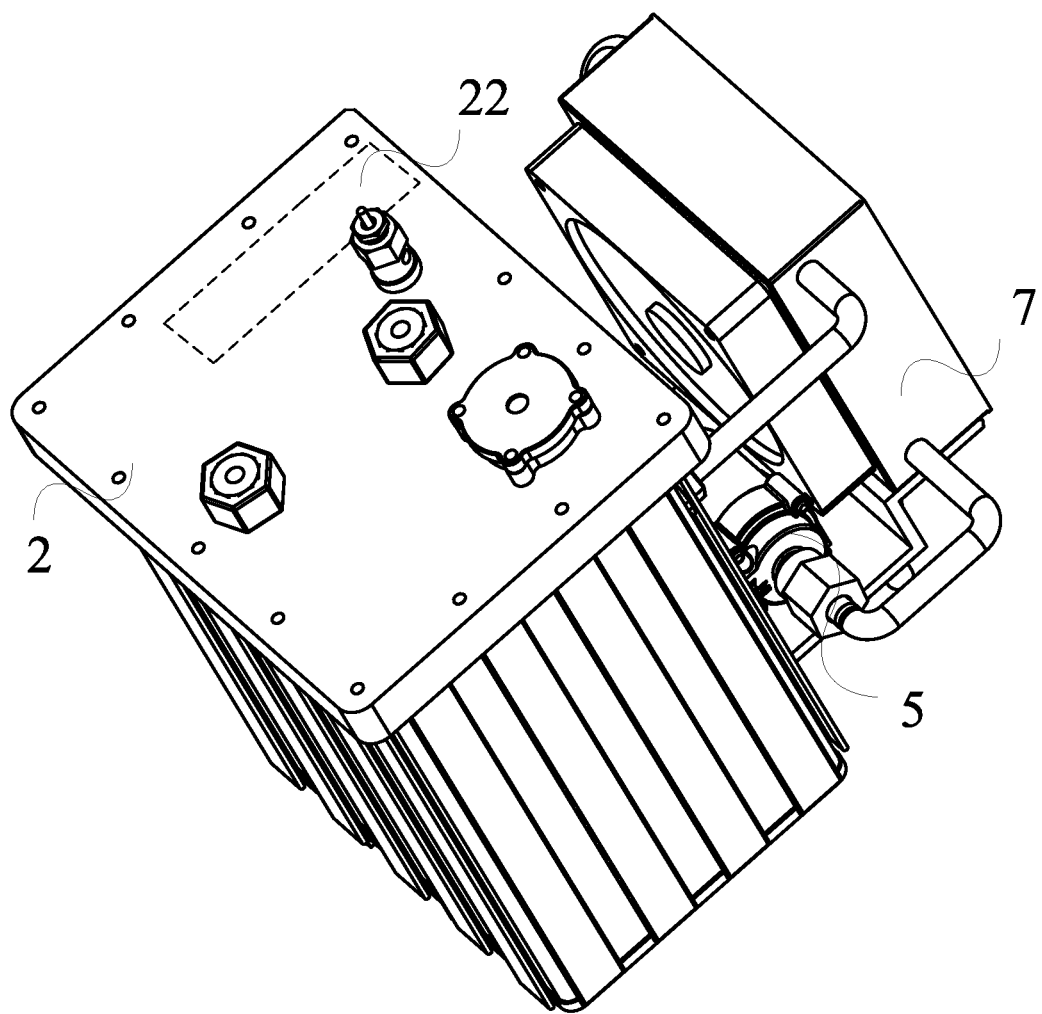
FIG. 17 shows a schematic diagram of the gas generator in the fifth embodiment of the present invention.

Please refer to FIG. 17. In the fourth embodiment, the present invention further provides a gas generator, which has function of controlling the temperature of the electrolyzed water and cooling down the electrolyzed water after generated hydrogen-oxygen mixed gas. In this embodiment, the gas generator 1 comprises an electrolysis device 3, a water pump 5, and a cooling device 7. The electrolysis device 3 contains an electrolyzed water W. The electrolysis device 3 is used to electrolyze the electrolyzed water W to generate a hydrogen-oxygen mixed gas G. The cooling device 7 is connected to the electrolysis device 3, used to cool down the electrolyzed water W after the hydrogen-oxygen mixed gas G is generated. The water pump 5 is connected between the cooling device 7 and the electrolysis device 3, used to enforce to circulate the electrolyzed water W.

Please refer to FIG. 17. FIG. 17 shows a schematic diagram of the gas generator in the fifth embodiment of the present invention. In the fifth embodiment, the gas generator 1 of the present invention further comprises a water tank 2. The water tank 2 has a first hollow portion 20 and a pipe 22 (shown by dotted line only in FIG. 17). The first hollow portion 20 of the water tank 2 contains electrolyzed water W. The electrolysis device 3 is disposed in the first hollow portion 20 of the water tank 2. The first hollow portion 20 is connected with the electrolysis device 3.

Additionally, in the sixth embodiment, the gas generator 1 of the present invention further comprises a nebulized gas mixing tank 4 (as shown in FIG. 15A). The nebulized gas mixing tank 4 can generates a nebulized gas G2 and be mixed with the hydrogen-oxygen mixed gas G to form a healthy gas for a user to breathe.

The following statement will explain the design of each element of the present invention respectively.

The designs of the structures of the water tank 2, the electrolysis device 3, the water pump 5, and the nebulized gas mixing tank 4 have been explained in the statements mentioned above, so unnecessary details will not be given again herein.

Figure 15B:
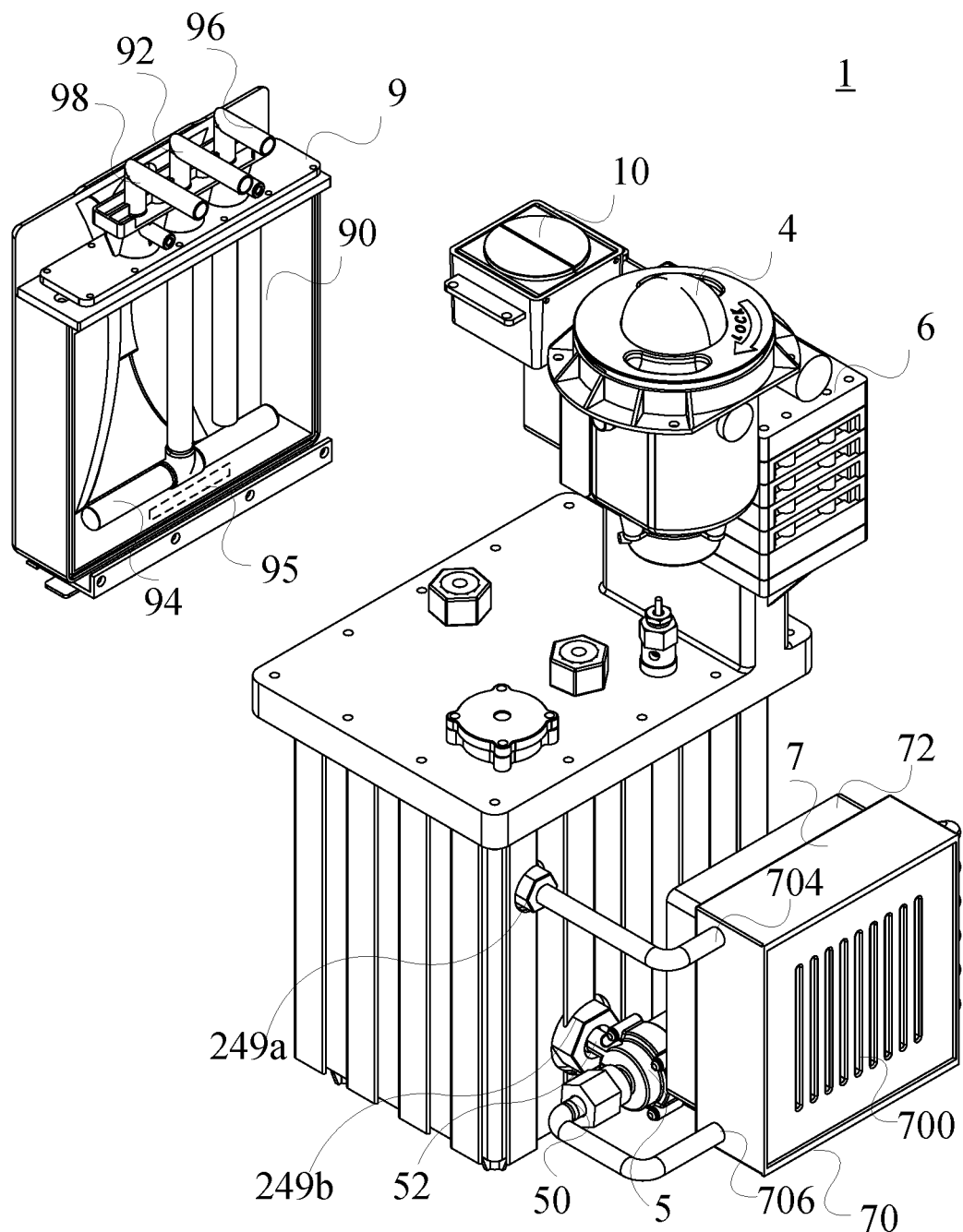

Please refer to FIG. 15A, FIG. 15B, and FIG. 17. In the fourth embodiment, the cooling device 7 of the present invention comprises a radiator 70 and a fan 72. The radiator 70 comprises a box 700 and a radiating tube 702. The radiating tube 702 is disposed in the box 700 of the radiator 70. The shape of the radiating tube 702 is a snake-shaped (not shown in the figure), used to increase the radiating area for increasing the radiating efficiency. But the present invention is not limited to the statement mentioned above. In practical application, the radiating tube 702 also can be a helix-shaped tube. Furthermore, in practical application, the radiating tube 702 can be formed by materials selected from a group consisting of silver, aluminum, copper, silver alloy, aluminum alloy, and copper alloy. Additionally, the radiator 70 comprises an inlet 704 and an outlet 706. The inlet 704 of the radiator 70 is connected with the two surfaces of the box 700 of the radiator 70 relative to the direction of the radiating tube 702. The outlet 706 of the radiator 70 is connected with the two surfaces of the box 700 of the radiator 70 relative to the direction of the radiating tube 702. Wherein, the inlet 704 and the outlet 706 of the radiator 70 are connected with each other through the radiating tube 702.

Additionally, in the fourth embodiment, the gas generator 1 of the present invention further comprises a microcomputer controller (not shown in the figure). The microcomputer controller is used to detect the temperature of the electrolyzed water W and control an inputting flow rate and an outputting flow rate of the water pump 5 according to the detected temperature of the electrolyzed water W. Furthermore, the microcomputer controller comprises a temperature sensor (not shown in the figure). The temperature sensor is used to detect the temperature of the electrolyzed water W contained in the electrolysis device 3. Furthermore, the microcomputer controller further comprises a flow quantity detector 82. The flow quantity detector 82 is used to detect the flow quantity of the hydrogen-oxygen mixed gas G, and further to control the quantity of the hydrogen-oxygen mixed gas G outputted from the electrolysis device 3. The flow quantity detector 82 can selectively cut off the electrical connection between the electrolysis device 3 and the power source (not shown in the figure).

After explaining the design of each element respectively, the following statement will describe the combination method and the application of each element.

In the water tank 2 and the electrolysis device 3 which is assembled completely, the electrolysis device 3 which is assembled completely is disposed in the first hollow portion 20 of the water tank 2, wherein the first hollow portion 20 of the water tank 2 is connected with the electrolysis device 3. Additionally, the combination method of the water tank 2 and the electrolysis device 3 has been explained in the statement mentioned above, so unnecessary details will not be given again herein.

In the water tank 2, the electrolysis device 3, the water pump 5, and the cooling device 7 which is assembled completely, the first hollow portion 20 of the water tank 2 is connected with the electrolysis device 3 (not shown in the figure). The cooling device 7 is connected to the water tank 2. The water pump 5 is connected between the radiator 7 and the water tank 2. But the present invention is not limited to the statement mentioned above. In practical application, the radiator 70 can be connected to the electrolysis device 3 directly, the water pump 5 can be connected between the radiator 7 and the water tank 2 directly, which means the water tank 2 of the gas generator of the present invention is unnecessary, or the electrolysis device 3 of the gas generator of the present invention is not needed to be disposed in the water tank 2.

The following statement will describe the connecting relationship between the water tank 2, the electrolysis device 3, and the water pump 5 which is assembled completely. Please refer to FIG. 15A and FIG. 15B. The outlet opening 249*a* of the water tank 2 which the electrolysis device 3 has been disposed in is connected with the inlet 704 of the radiator 70 of the cooling device 7. The outlet 706 of the radiator 70 of the cooling device 7 is connected with the inlet pipe 50 of the water pump 5. The outlet pipe 52 of the water pump 5 is connected with the outlet opening 249*b* of the water tank 2. But the present invention is not limited to the connecting relationship mentioned above. In practical application, the outlet opening 249*a* of the water tank 2 which the electrolysis device 3 has been disposed in can be connected with the inlet pipe 50 of the water pump 5, the outlet pipe 52 of the water pump 5 can be connected with the inlet 704 of the radiator 70 of the cooling device 7, and the outlet 706 of the radiator 70 of the cooling device 7 can be connected with the inlet opening 249*b* of the water tank 2.

In practical application, an electrolyzed water W is contained in the water tank 2. The electrolysis device 3 is disposed in the water tank 2, used to electrolyze the electrolyzed water W to generate a hydrogen-oxygen mixed gas G. The hydrogen-oxygen mixed gas G generated in the electrode channel S1 is outputted to the first hollow portion 20 through the corresponding upper via 360 of the pad 36 and the corresponding first channel 370 of the upper cover body 37. The hydrogen-oxygen mixed gas G inputted into the first hollow portion 20 is further outputted through the pipe 22 of the water tank 2 for a user to breathe. But the present invention is not limited to the statement mentioned above. In practical application, the hydrogen-oxygen mixed gas G outputted from the first hollow portion 20 can further be mixed with the nebulized gas G2 generated by the nebulized gas mixing tank 4 to form a healthy gas for a user to breathe.

Additionally, when the electrolysis device 3 pauses to electrolyze the electrolyzed water W for generating the hydrogen-oxygen mixed gas G, the pipe 22 can be used to recharge the electrolyzed water W for allowing the first hollow portion 20 and the electrolysis device 3 to be filled with the electrolyzed water W. The electrolyzed water W recharged in the first hollow portion 20 can be outputted to the corresponding electrode channel S1 through the second channel 380 of the lower cover body 38 of the electrolysis device 3 and the plurality of lower via 3202, for providing the needed electrolyzed water W while the electrolysis device 3 is electrolyzing.

Additionally, the water tank 2, the electrolysis device 3, the water pump 5, and the cooling device 7 are connected with each others. In application, the electrolyzed water W after the hydrogen-oxygen mixed gas G is generated can be enforced to be outputted from the outlet opening 249*a* of the water tank 2 to the inlet 704 of the radiator 70 of the cooling device 7 through the water pump 5. Then, the electrolyzed water W can be cooled down in the radiating tube 702 of the radiator 70. The cooled electrolyzed water W can be enforced to be outputted to the inlet pipe 50 of the water pump 5 by water pump 5 through the outlet 706 of the radiator 70. Furthermore, the electrolyzed water W can be enforced to be inputted into the inlet opening 249*b* of the water tank 2 by the water pump 5 through the outlet pipe 52 of the water pump 5. Therefore, the gas generator of the present invention can cool down the electrolyzed water after the hydrogen-oxygen mixed gas is generated through the cooling device, and enforce to circulate the electrolyzed water through the water pump to achieve the goal of heat radiation. Wherein, the temperature of the electrolyzed water contained in the electrolysis device is a normal electrolyzed temperature. In practical application, the temperature of the electrolyzed water W contained in the electrolysis device 3 can be between 55° C. to 65° C.

Additionally, the microcomputer controller 8 is coupled to the water pump 5, used to detect the temperature of the electrolyzed water W and control an inputting flow rate and an outputting flow rate of the water pump 5 according to the detected temperature of the electrolyzed water W. In practical application, when the temperature of the electrolyzed water W sensed by the temperature sensor 80 is higher than a predetermined temperature, the information that the temperature is too high will be sent back to the microcomputer controller 8. Then, the microcomputer controller 8 will further control the water pump 5 for speeding up the flow rate of the circulation of the electrolyzed water W to allow the temperature of the electrolyzed water to be decreased to the range of the predetermined temperature. However, when the temperature of the electrolyzed water W sensed by the temperature sensor 80 is lower than a predetermined temperature, the information that the temperature is too low will be sent back to the microcomputer controller 8. Then, the microcomputer controller 8 will further control the water pump 5 for slowing down the flow rate of the circulation of the electrolyzed water W to allow the temperature of the electrolyzed water to be increased to the range of the predetermined temperature. Wherein, the predetermined temperature is the temperature which can provide optimal electrolytic efficiency. In this embodiment, the predetermined temperature is a normal electrolyzed temperature. In practical application, the normal electrolyzed temperature is between 55° C. to 65° C.

To summarize the statements mentioned above, the priority of the present invention is to provide a gas generator, comprising an electrolysis device, a cooling device, and a water pump. The gas generator of the present invention can cool down the electrolyzed water after the hydrogen-oxygen mixed gas is generated through the cooling device, and enforce to circulate the electrolyzed water through the water pump to achieve the goal of heat radiation. Meanwhile, the present invention can allow the temperature of the electrolyzed water to be in a temperature range which can provide an optimal electrolytic efficiency for effectively electrolyzing the electrolyzed water to generate hydrogen-oxygen mixed gas, to solve the energy consumption problems.

Figure 9A:
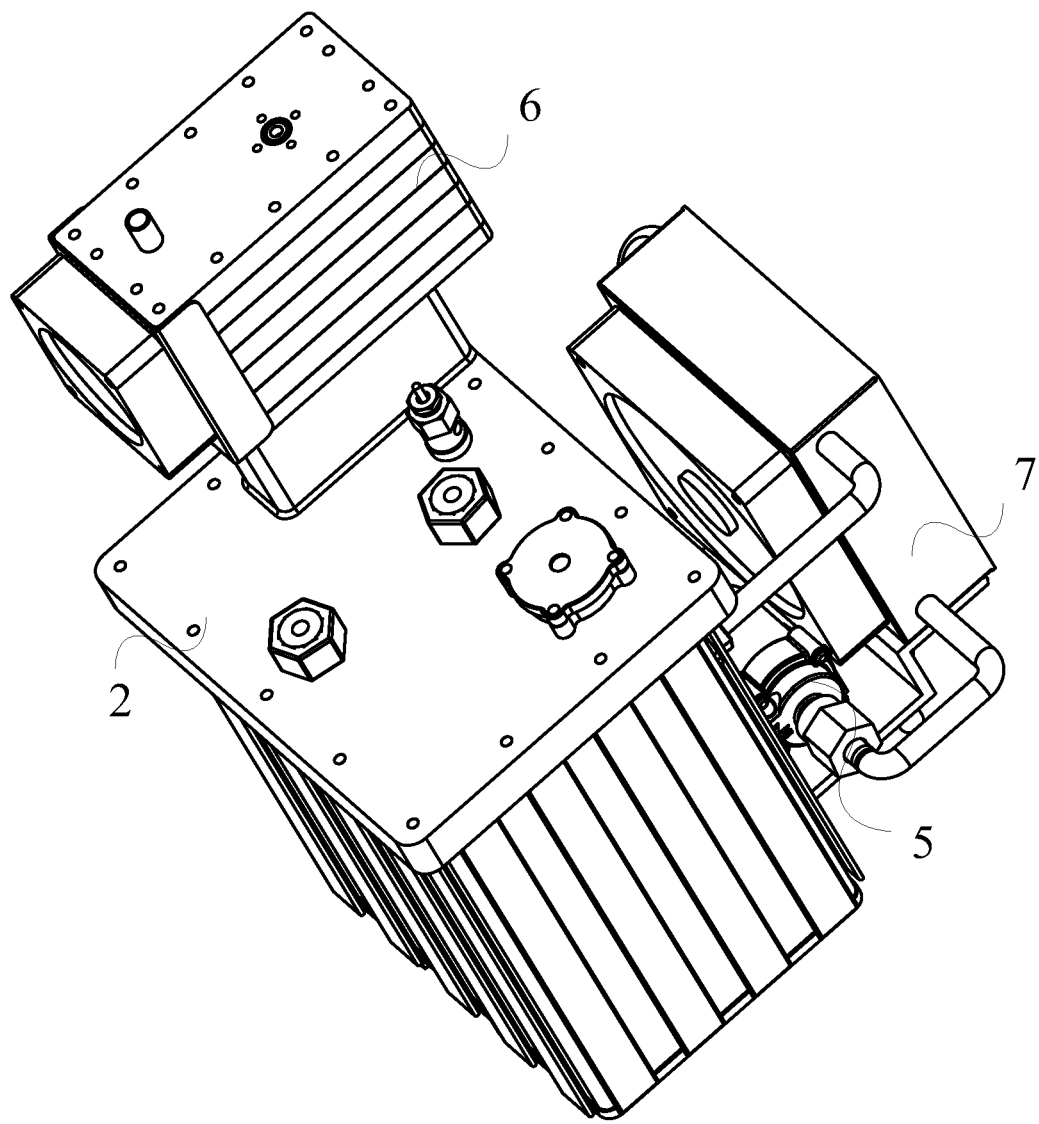
FIG. 9A and FIG. 9B show a schematic diagram of the gas generator in the tenth embodiment with different visual angles of the present invention.
Figure 9B:
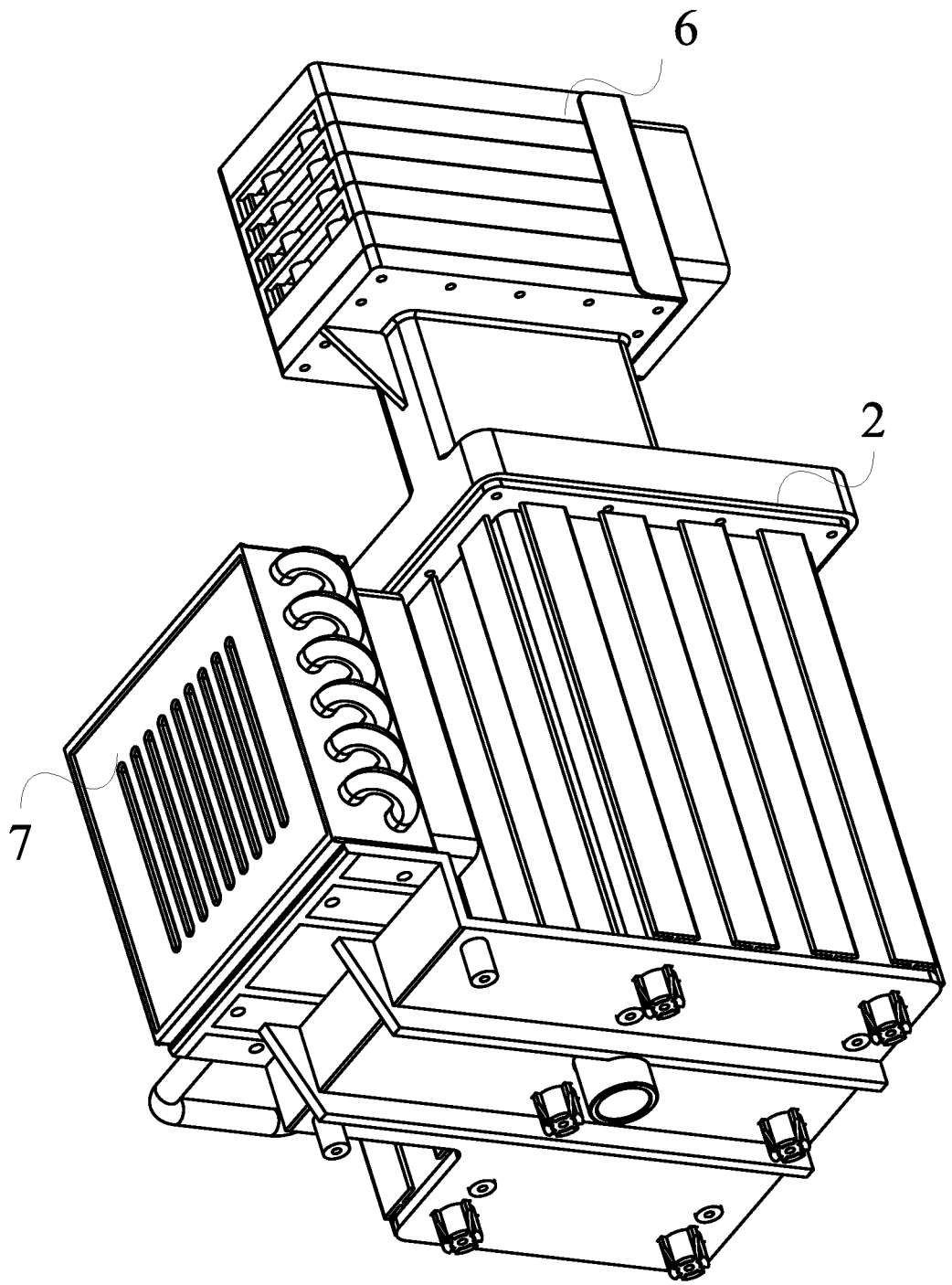

Please refer to FIG. 9A and FIG. 9B. The present invention further provides a gas generator, which is a gas generator having function of filtering. In the seventh embodiment, the gas generator 1 comprises an electrolysis device 3 and a condense filter 6. The electrolysis device 3 contains an electrolyzed water W (not shown in the figure). The electrolysis device 3 is used to electrolyze the electrolyzed water W to generate a hydrogen-oxygen mixed gas G. The condense filter 6 is connected to the electrolysis device 3, used to condense the hydrogen-oxygen mixed gas G and filter out the impurities in the hydrogen-oxygen mixed gas G. Wherein, when the electrolysis device 3 pauses to electrolyze the electrolyzed water W for generating the hydrogen-oxygen mixed gas G, the condense filter 6 can be used to input a recharged water W2 (not shown in the figure), and the impurities can be flushed back to the electrolysis device 3 via the recharged water W2 through the condense filter 6.

Additionally, in the eighth embodiment, the gas generator 1 of the present invention further comprises a water tank 2. The water tank 2 has a first hollow portion 20. The first hollow portion 20 of the water tank 2 contains the electrolyzed water W. The electrolysis device 3 is disposed in the first hollow portion 20 of the water tank 2. The first hollow portion 20 is connected with the electrolysis device 3.

Additionally, in the ninth embodiment, the gas generator 1 of the present invention further comprises a nebulized gas mixing tank 4 (as shown in FIG. 15A). The nebulized gas mixing tank 4 can be used to receive the filtered hydrogen-oxygen mixed gas G. The nebulized gas mixing tank 4 can generate nebulized gas G2 and be mixed with the filtered hydrogen-oxygen mixed gas G to form a healthy gas for a user to breathe.

Please refer to FIG. 9A and FIG. 9B. FIG. 9A and FIG. 9B show a schematic diagram of the gas generator in the tenth embodiment with different visual angles of the present invention. In the tenth embodiment, the gas generator 1 of the present invention further comprises a water pump 5 and a cooling device 7.

The following statement will explain the design of each element of the present invention respectively.

The designs of the structures of the water tank 2, the electrolysis device 3, and the nebulized gas mixing tank 4 have been explained in the statement mentioned above, so unnecessary details will not be given again herein.

Please refer to FIG. 10A, FIG. 10B, FIG. 11, FIG. 12, FIG. 13, FIG. 14A, and FIG. 14B. The condense filter 6 of the present invention has a gas inlet via 60 and a gas outlet via 62. The gas inlet via 60 can be connected to the electrolysis device 3, used to receive the hydrogen-oxygen mixed gas. The gas outlet via 62 is used to output the filtered hydrogen-oxygen mixed gas G. Additionally, the condense filter 6 of the present invention comprises a plurality of condense plate 64. Each condense plate 64 has a channel 640. The channel 640*a* of the condense plate 64 is connected with the adjacent channel 640*a* of the condense plate 64 to form a circulating channel 640 for the hydrogen-oxygen mixed gas G to flow through, for condensing the hydrogen-oxygen mixed gas G. The gas inlet via 60 and the gas outlet via 62 can be connected with each other through the circulating channel 640. Additionally, an active carbon fiber is disposed in the channel 640*a*, used to filter the impurities in the hydrogen-oxygen mixed gas G. A filter material is further disposed on the channel 640*a*, wherein the filter material is selected from a group consisting of ceramics, quartz, kieselguhr, meerschaum, and the combination thereof. The filter material can be further used to filter the impurities in the hydrogen-oxygen mixed gas G. Wherein, the impurities is electrolyte in the electrolyzed water W, which is sodium hydroxide. But the present invention is not limited to the statement mentioned above. In practical application, the impurities can be calcium carbonate or sodium chloride. Additionally, the gas inlet via 60 of the present invention is formed by a filter gauze 600 and a cover of the filter gauze 602. The filter gauze 600 and the cover of the filter gauze 602 can be connected to the electrolysis device 3, used to receive the hydrogen-oxygen mixed gas G, and preliminarily filter the hydrogen-oxygen mixed gas G. Wherein, the electrolysis device 3 is contained in the water tank 2 to further be connected with the condense filter 6.

After explaining the design of each element in the statement mentioned above, the following statement will describe the combination method and the application of each element of the present invention.

In the electrolysis device 3 which is assembled completely, a plurality of electrodes are disposed respectively on the space in the electrolysis tank 32. The pad 36 is disposed on the upper surface of each electrode 34. The upper cover body 37 is covered on the other end of the pad 36 relative to the electrolysis tank 32. The lower cover body 38 is covered on the other end of the lower surface of the electrolysis tank 32 relative to the upper cover body 37.

In the water tank 2 and the electrolysis device 3 which is assembled completely, the positive plate 342 and the negative plate 340 of the electrolysis device 3 are fixed on the cover body 26 of the water tank 2 respectively through two electrode columns 33. And the detector (such as flow quantity detector 82) are passed through the plurality of cover holes 261 of the cover body 26 of the water tank 2 and disposed on the cover body 26 of the water tank 2. The seal 28 is disposed on the tank body 24 of the water tank 2. The seal 28 and the tank body 24 of the water tank 2 are embedded with each other through the third embed structure 282 of the seal 28 and the first embed structure 246 of the tank body 24 of the water tank 2. The first side margin 248 of the tank body 24 of the water tank 2 is covered in the second hollow portion 264 of the cover body 26 of the water tank 2 through the second opening portion 266 of the cover body 26 of the water tank 2, for allowing the tank body 24 of the water tank 2 and the cover body 26 of the water tank 2 to be combined tightly, and allowing the electrolysis device 3 to be disposed in the midair in the water tank 2. Wherein, the first hollow portion 20 of the water tank 2 is connected with the electrolysis device 3.

In the water tank 2, the electrolysis device 3, and the condense filter 6 which is assembled completely, the water tank 2 which the electrolysis device 3 has been disposed in is connected with the condense filter 6 through the connection between the pipe 22 of the water tank 2 and the gas inlet via 60 of the condense filter 6. Additionally, the nebulized gas mixing tank 4 can be connected to the gas outlet via 62 of the condense filter 6.

In practical application, the water tank 2 contains an electrolyzed water W. The electrolysis device 3 is disposed in the water tank 2, used to electrolyze the electrolyzed water W to generate a hydrogen-oxygen mixed gas G. The hydrogen-oxygen mixed gas G generated in the electrode channel S1 is outputted into the first hollow portion 20 through the corresponding upper via 360 of the pad 36 and the corresponding first channel 370 of the upper cover body 37. The hydrogen-oxygen mixed gas G inputted into the first hollow portion 20 is further outputted through the pipe 22 of the water tank 2. The hydrogen-oxygen mixed gas G outputted from the pipe 22 of the water tank 2 can be inputted into the condense filter 6 through the gas inlet via 60 of the condense filter 6 to be condensed and filtered. The hydrogen-oxygen mixed gas G inputted through the gas inlet via 60 of the condense filter 6 will pass through the filter gauze 600 and the cover of the filter gauze 602 first to be preliminarily filtered. Then, the hydrogen-oxygen mixed gas G which has been filtered preliminarily will further be inputted into the circulating channel 640 to be condensed. Meanwhile, the hydrogen-oxygen mixed gas G can be filtered through the active carbon fiber and the filter material disposed in the channel 640a. The impurities will be adhered in the circulating channel 640. The filtered hydrogen-oxygen mixed gas G can be outputted through the gas outlet via 62 of the condense filter 6 for the user to breathe. But the present invention is not limited to the statement mentioned above. In practical application, the hydrogen-oxygen mixed gas G outputted from the condense filter 6 can further be mixed with the nebulized gas G2 generated by the nebulized gas mixing tank 4 to form a healthy gas for a user to breath Additionally, when the electrolysis device 3 pauses to electrolyze the electrolyzed water W for generating the hydrogen-oxygen mixed gas G, the gas outlet via 62 of the condense filter 6 can be used to recharge the electrolyzed water W. The recharged water W2 which is recharged from the gas outlet via 62 of the condense filter 6 can be outputted into the first hollow portion 20 of the water tank 2 through the pipe 22 which is connected with the gas outlet via 62. The electrolyzed water W recharged in the first hollow portion 20 can be outputted into the corresponding electrode channel S1 through the second channel 380 of the lower cover body 38 of the electrolysis device and the plurality of lower vias 3202 for providing the needed electrolyzed water W when the electrolysis device 3 is electrolyzing. Meanwhile, the impurities adhered in the circulating channel 640 of the condense filter 6 can be flushed back to the water tank 2 which the electrolysis device 3 has been disposed in by the recharged water W2 mentioned above through the gas inlet via 60 and the pipe 22.

Additionally, the flow quantity detector 82 which is coupled to the electrolysis device 3 can detect the flow quantity of the hydrogen-oxygen mixed gas G. Wherein, the generated flow rate of the hydrogen-oxygen mixed gas G of the gas generator 1 is between 0.01 L/min to 12 L/min.

To summarize the statement mentioned above, the priority of the present invention is to provide a gas generator, a comprising electrolysis device and a condense filter. In the gas generator of the present invention, the hydrogen-oxygen mixed gas generated by the electrolysis device can be condensed and filtered through the condense filter, for providing a hydrogen-oxygen mixed gas which is appropriate for humans to breathe. Meanwhile, through the design of the present invention, the electrolyte can be flushed back to the electrolysis device when recharging water, used to decrease the consumption of the electrolyte and avoid the electrolyte to block the condense filter.

Figure 16:
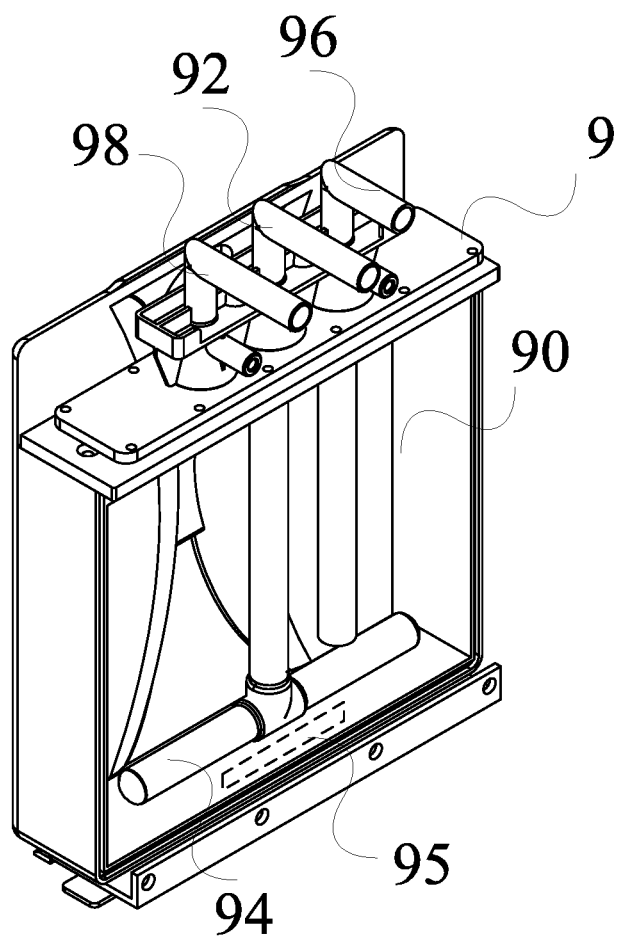
FIG. 16 shows a schematic diagram of the present invention which only has the humidification device in the embodiment shown in FIG. 15A.

Please refer to FIG. 15A, FIG. 15B, and FIG. 16. In the eleventh embodiment, the present invention further provides a gas generator having the function of humidification. The gas generator 1 comprises an electrolysis device 3 and a humidification device 9. The electrolysis device 3 contains the electrolyzed water W, used to electrolyze the electrolyzed water W to generate a hydrogen-oxygen mixed gas G. The humidification device 9 is connected to the electrolysis device 3, used to receive and humidify the hydrogen-oxygen mixed gas G.

Additionally, in the twelfth embodiment, the gas generator 1 of the present invention further comprises a condense filter 6. The condense filter 6 can be disposed between the electrolysis device 3 and the humidification device 9, used to condense and filter the hydrogen-oxygen mixed gas G generated by the electrolysis device 3.

Additionally, in the thirteenth embodiment, the gas generator 1 of the present invention further comprises a nebulized gas mixing tank 4. The nebulized gas mixing tank 4 can be used to receive the filtered hydrogen-oxygen mixed gas G. The nebulized gas mixing tank 4 can generate nebulized gas G2 and be mixed with the hydrogen-oxygen mixed gas G to form a healthy gas for a user to breathe. But the present invention is not limited to the statement mentioned above. In another embodiment, the nebulized gas mixing tank 4 of the present invention can be a hand-held atomize device (not shown in the figure). The hand-held atomize device can be connected to the humidification device 9, used to receive the humidified hydrogen-oxygen mixed gas. The hand-held atomize device generates a nebulized gas and is mixed with the humidified hydrogen-oxygen to form a healthy gas for a user to breathe. Wherein, the nebulized gas is selected from a group consisting of water vapor, nebulized medicinal liquid, evaporated essential oil, and the combination thereof. In practical application, the hand-held atomize device has a pressed structure. The user can press the pressed structure of the hand-held atomize device for outputting an appropriate quantity of healthy gas to breathe.

Please refer to FIG. 15A, and FIG. 15B. FIG. 15A and FIG. 15B show a schematic diagram of the gas generator in the fourteenth embodiment with different visual angles of the present invention. Additionally, in the fourteenth embodiment, the gas generator 1 of the present invention further comprises a water tank 2, a water pump 5, a cooling device 7, and a gas output device 10. The gas output device 10 can be used to output the healthy gas for a user to breathe, wherein the healthy gas is the mixture of humidified hydrogen-oxygen mixed gas G and nebulized gas G2.

The following statement will respectively explain the design of each element of the present invention.

The designs of the structures of the condense filter 6 and the nebulized gas mixing tank 4 have been explained in the above mentioned statements, so unnecessary details will not be given again herein.

The humidification device 9 of the present invention comprises a hollow body 90, a second pipe 92, at least one outputting pipe 94, an oscillation device 95 (shown by dotted line only in FIG. 15), a third pipe 96, and a fourth pipe 98. The hollow body 90 can be used to contain the recharged water W2. The second pipe 92 is disposed on the hollow body 90, which can be used to connect with the electrolysis device 3 (not shown in the figure). The outputting pipe 94 is disposed in the hollow body 90 and connected to the second pipe 92. The second pipe 92 is connected with the two outputting pipe 94 to form a T-shaped structure. But the present invention is not limited to the statement mentioned above. In practical application, the connection between the second pipe and the outputting pipe can be adjusted according to the using condition. Additionally, the surfaces of the two outputting pipe 94 have a plurality via, wherein the via mentioned above has a scale diameter. In practical application, the scale of the via can be between 2 meters to 10 meters. But the present invention is not limited to the statement mentioned above. The scale of the via can be adjusted according to the requirement of users. A rubber bung is disposed on the end of the two outputting pipe 94 which is connected to the second pipe 92, used to output the hydrogen-oxygen mixed gas G received by the second pipe 92 to the hollow body 90 through the plurality of via (not shown in the figure) of the two outputting pipe 94. But the present invention is not limited to the statement mentioned above. In practical application, the design of the end of the two outputting pipe 94 which is connected to the second pipe 92 can be enclosed. The oscillation device 95 can be disposed in the hollow body 90 and beneath the outputting pipe 94 to oscillate recharged water. The oscillation device 95 can comprise an ultrasonic wave oscillation device, used to oscillate the recharged water contained in the hollow body 90. In practical application, the oscillation device is not limited to the ultrasonic wave oscillation device mentioned in this embodiment, and the position is not limited to the spot shown in FIG. 15B. Any device which is disposed in the hollow body and can be used to oscillate or agitate the water for effectively dispersing the hydrogen-oxygen mixed gas to form micro bubbles is comprised in the definition of the oscillation device of the present invention. For example, the oscillation device 95 also can comprise a centrifugal blade and s driving motor which are connected to the centrifugal blade. The driving motor can drive the centrifugal blade to rotate for generating swirl in the water to help the hydrogen of the hydrogen-oxygen mixed gas to be effectively distributed in the water to form hydrogen water. The oscillation device 95 can comprise an ultrasonic wave oscillation device, a centrifugal blade, and a driving motor mentioned above at the same time for generating the hydrogen water more effectively. The third pipe 96 can be disposed on the hollow body 90, used to output the hydrogen water H or input the recharged water W2. In practical application, the third pipe can be connected to a pilot via. Through the third pipe and the pilot via, the hydrogen water H can be outputted or the recharged water W2 can be inputted. The fourth pipe 98 can be disposed on the hollow body 90, used to output the humidified hydrogen-oxygen mixed gas G.

Additionally, in another embodiment, the gas generator 1 of the present invention further comprises a water tank 2. The water tank 2 has a first hollow portion 20. The first hollow portion 20 of the water tank 2 contains the electrolyzed water W. The electrolysis device 3 is disposed in the first hollow portion 20 of the water tank 2. The first hollow portion 20 is connected with the electrolysis device 3. Additionally, the humidification device 9 of the present invention can further comprise a second water pump (not shown in the figure). The second water pump can be disposed on the cover body 26 of the water tank 2 and connected to the first hollow portion 20, used to draw gas in the water tank 2 to form a negative pressure.

After explaining the design of each element in the statements mentioned above, the following statement will describe the combination method and the application of each element of the gas generator of the present invention.

In the electrolysis device 3 which is assembled completely, a plurality of electrodes are disposed on the space in the electrolysis tank 32. The pad 36 is disposed on the upper surface of each electrode. The upper cover body 37 is covered on the other end of the pad 36 relative to the electrolysis tank 32. The lower cover body 38 is covered on the other end of the lower surface of the electrolysis tank 32 relative to the upper cover body 37.

In the water tank 2 and the electrolysis device 3 which is assembled completely, the positive plate 342 and the negative plate 340 of the electrolysis device 3 are fixed on the cover body 26 of the water tank 2 through the two electrode columns 33 respectively. And the detector (such as flow quantity detector 82) are passed through the plurality of cover holes 261 of the cover body 26 of the water tank 2 and disposed on the cover body 26 of the water tank 2. The seal 28 is disposed on the tank body 24 of the water tank 2. The seal 28 and the tank body 24 of the water tank 2 are embedded with each other through the third embed structure 282 of the seal 28 and the first embed structure 246 of the tank body 24 of the water tank 2. The first side margin 248 of the tank body 24 of the water tank 2 is covered in the second hollow portion 264 of the cover body 26 of the water tank 2 through the second opening portion 266 of the cover body 26 of the water tank 2, for allowing the tank body 24 of the water tank 2 and the cover body 26 of the water tank 2 to be combined tightly, and allowing the electrolysis device 3 to be disposed in the midair in the water tank 2. Wherein, the first hollow portion 20 of the water tank 2 is connected with the electrolysis device 3.

In the water tank 2, the electrolysis device 3, the condense filter 6, and the humidification device 9 which is assembled completely, the water tank 2 which the electrolysis device 3 has been disposed in is connected with the condense filter 6 through the connection between the pipe 22 of the water tank 2 and the gas inlet via 60 of the condense filter 6. Additionally, the condense filter 6 and the humidification device 9 are connected with the water tank through the connection between the gas outlet via 60 of the condense filter 6 and the second pipe 92 of the humidification device 9. Furthermore, in the thirteenth embodiment, the nebulized gas mixing tank 4 can be connected to the fourth pipe 98 of the humidification device 9.

In practical application, the water tank 2 contains an electrolyzed water W. The electrolysis device 3 is disposed in the water tank 2, used to electrolyze the electrolyzed water W to generate a hydrogen-oxygen mixed gas G. The hydrogen-oxygen mixed gas G generated in the electrode channel S1 is outputted into the first hollow portion 20 through the corresponding upper via 360 of the pad 36 and the corresponding first channel 370 of the upper cover body 37. The hydrogen-oxygen mixed gas G inputted into the first hollow portion 20 is further outputted through the pipe 22 of the water tank 2. The hydrogen-oxygen mixed gas G outputted from the pipe 22 of the water tank 2 can be inputted into the condense filter 6 through the gas inlet via 60 of the condense filter 6 to be condensed and filtered. The hydrogen-oxygen mixed gas G inputted through the gas inlet via 60 of the condense filter 6 will pass through the filter gauze 600 and the cover of the filter gauze 602 first to be preliminarily filtered. Then, the hydrogen-oxygen mixed gas G which has been filtered preliminarily will further be inputted into the circulating channel 640 to be condensed. Meanwhile, the hydrogen-oxygen mixed gas G can be filtered through the active carbon fiber and the filter material disposed in the channel 640a. The impurities will be adhered in the circulating channel 640. The filtered hydrogen-oxygen mixed gas G can be outputted through the gas outlet via 62 of the condense filter 6.

Additionally, the filtered hydrogen-oxygen mixed gas G can be outputted to the humidification device 9 through the second pipe 92 which is connected to the gas outlet via 62. The filtered hydrogen-oxygen mixed gas G received by the second pipe 92 can be outputted to the hollow body 90 through the plurality of vias of the two outputting pipe 94. In practical application, the plurality of vias on the surface of the outputting pipe 94 can be used to thin the hydrogen-oxygen mixed gas which is inputted into the humidification device for forming thin bubbles which can be dissolved easily. Meanwhile, the recharged water contained in the humidification device 9 is oscillated by the oscillation device 95, used to allow the gas to be dissolved in the oscillated recharged water easily. Wherein, the hydrogen-oxygen mixed gas G outputted from the via mentioned above can be humidified by the recharged water which is oscillated by the oscillation device 95 to generate humidified hydrogen-oxygen mixed gas for a user to breathe. But the present invention is not limited to the statement mentioned above. In practical application, the humidified hydrogen-oxygen mixed gas G outputted from the humidification device 9 can further be mixed with the nebulized gas G2 generated by the nebulized gas mixing tank 4, to form healthy gas for a user to breathe. Additionally, the hydrogen-oxygen mixed gas G, which is outputted from the outputting pipe which has via on the surface thereof, also can be combined with the recharged water which is oscillated by the oscillation device 95 to generate a hydrogen water H. More particularly, the hydrogen-oxygen mixed gas G, which is outputted from the outputting pipe which has via on the surface thereof, is a thin bubble which can be dissolved easily. And the recharged water which is oscillated by the oscillation device 95 is recharged water which allows gas to be dissolved easily. Therefore, by means of the gas generator of the present invention, the hydrogen water H with high concentration of hydrogen-oxygen mixed gas can be generated.

Additionally, when the electrolysis device 3 pauses to electrolyze the electrolyzed water W for generating the hydrogen-oxygen mixed gas G, the second water pump can be used to draw the gas in the water tank 2 to form a negative pressure. The recharged water W2 which is inputted through the third pipe 96 can be outputted back to the water tank 2 which the electrolysis device 3 has been disposed in by the humidification device 9 through the negative pressure mentioned above. More particularly, the recharged water can be inputted into the condense filter 6 from the humidification device 9 through the combination between the second pipe 92 of the humidification device 9 and the gas outlet via 62 of the condense filter 6. Additionally, the impurities adhered in the circulating channel 640 of the condense filter 6 can be flushed back to the water tank 2 which the electrolysis device 3 has been disposed in via the recharged water through the gas inlet via 60 and the pipe 22 mentioned above, used to recover the filter ability of the circulating channel, avoid the circulating channel to be blocked or corroded, and decrease the consumption of the electrolyte. In practical application, the present invention utilizes the recharged water to allow the impurities (which means electrolytes) to be flushed back to the water tank 2 which the electrolysis device 3 has been disposed in, which can be used to provide the needed electrolyzed water W while the electrolysis device 3 is electrolyzing. Additionally, the recharged water W recharged in the first hollow portion 20 of the water tank 2 can be outputted to the corresponding electrode channel S1 through the second channel 380 of the lower cover body 38 of the electrolysis device 3 and the plurality of lower vias 3202, used to provide the needed electrolyzed water W while the electrolysis device 3 is electrolyzing.

To summarize the statement mentioned above, the priority of the present invention is to provide a gas generator, a comprising electrolysis device and a humidification device. In the gas generator of the present invention, the hydrogen-oxygen mixed gas generated by the electrolysis device can be humidified by the humidification device for a user to breathe. Additionally, the hydrogen-oxygen mixed gas generated by the electrolysis device can further generate hydrogen water H with high concentration of hydrogen-oxygen mixed gas through the humidification device. In practical application, the concentration of hydrogen-oxygen mixed gas of the hydrogen water can be adjusted according to the requirement of the user. Furthermore, the design of the present invention can be used to recharge recharged water. Meanwhile, the electrolyte will be flushed back to the electrolysis device to recover the filter ability of the circulating channel, avoid the circulating channel to be blocked or corroded, and decrease the consumption of the electrolyte.

Figure 18A:
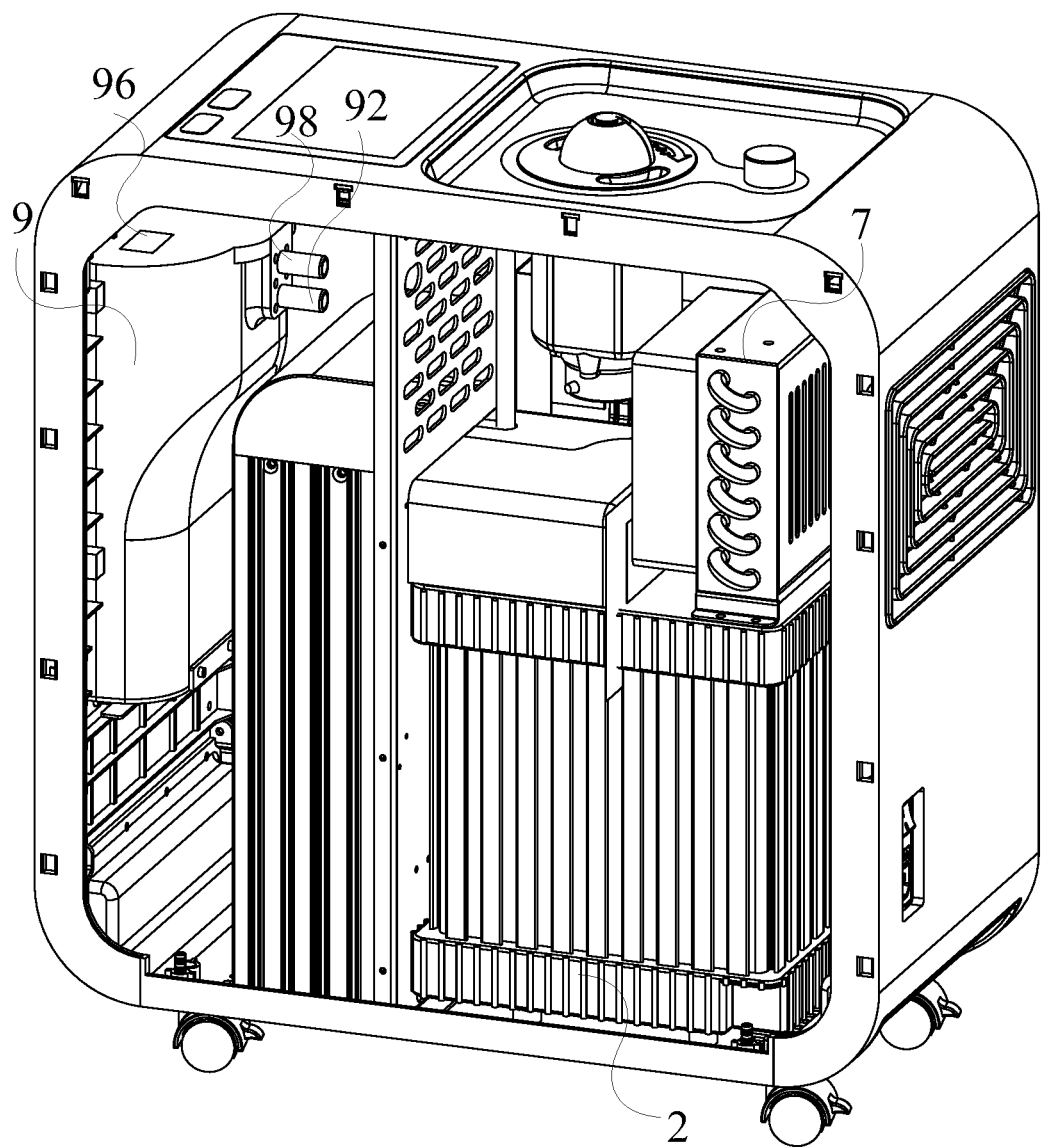
FIG. 18A and FIG. 18B show a schematic diagram of the gas generator in the fifteenth embodiment with different visual angle of the present invention.
Figure 18B:
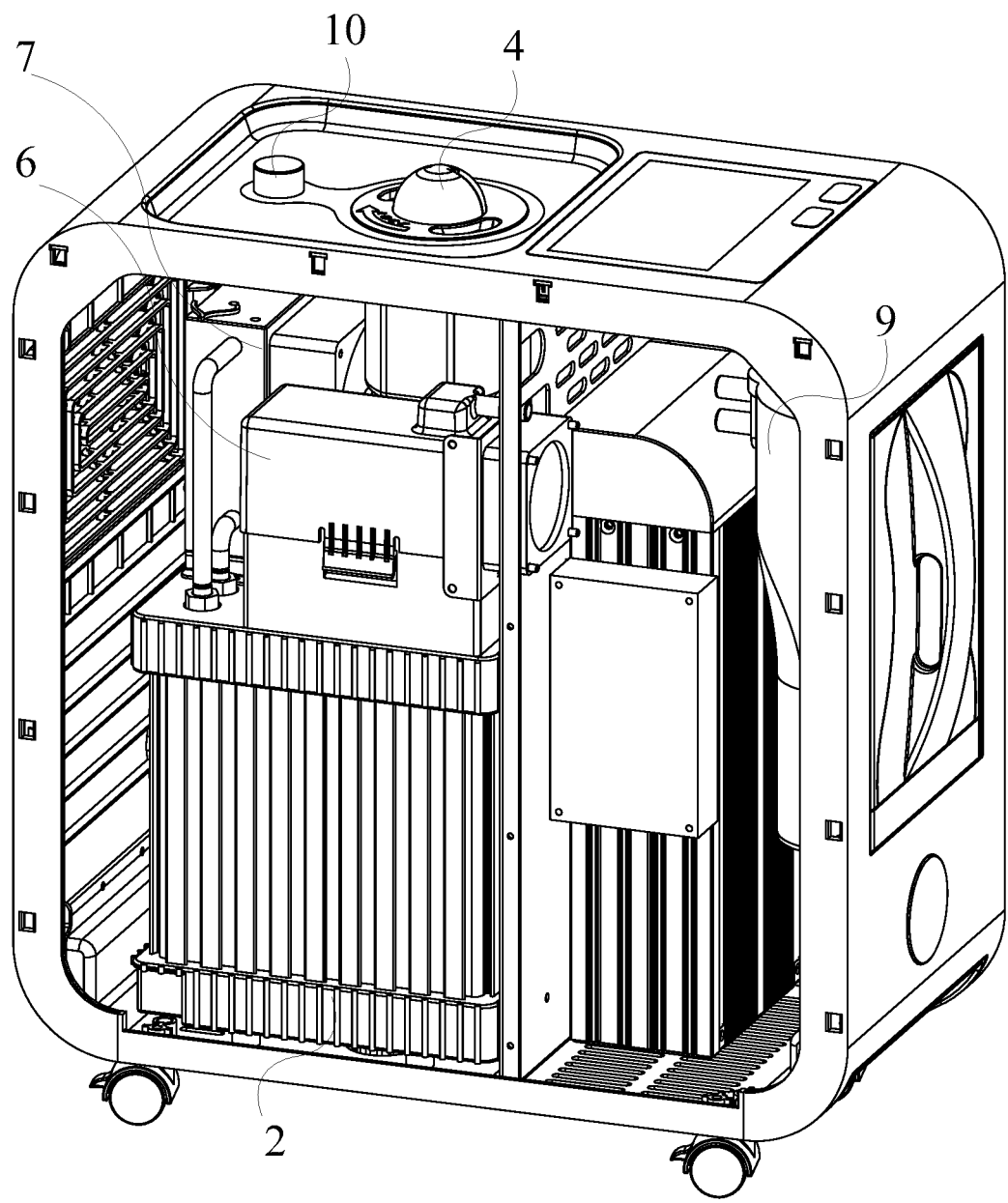
Figure 19:
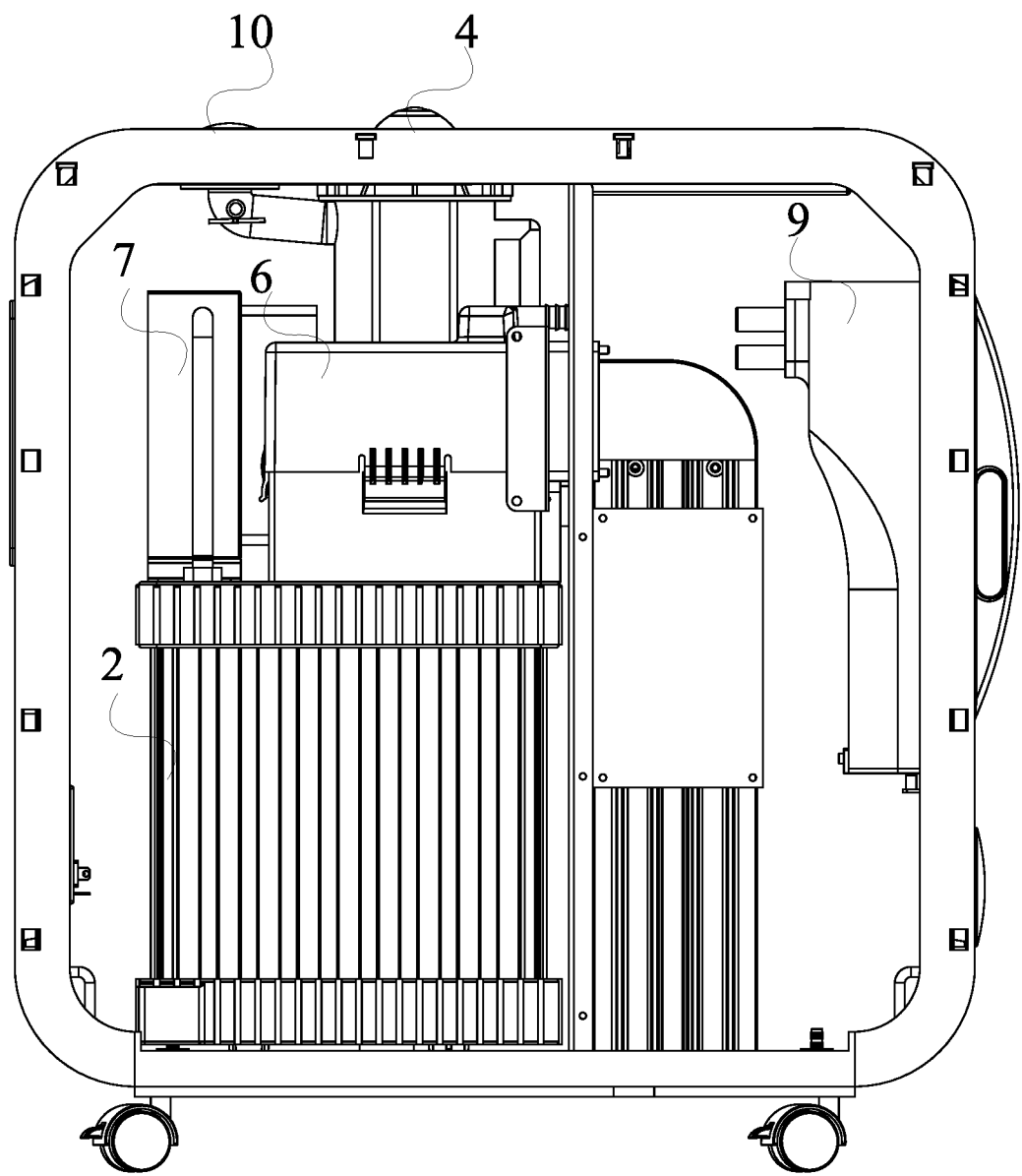
FIG. 19 shows a back view diagram of the gas generator in the embodiment shown in FIG. 18A of the present invention.
Figure 20A:
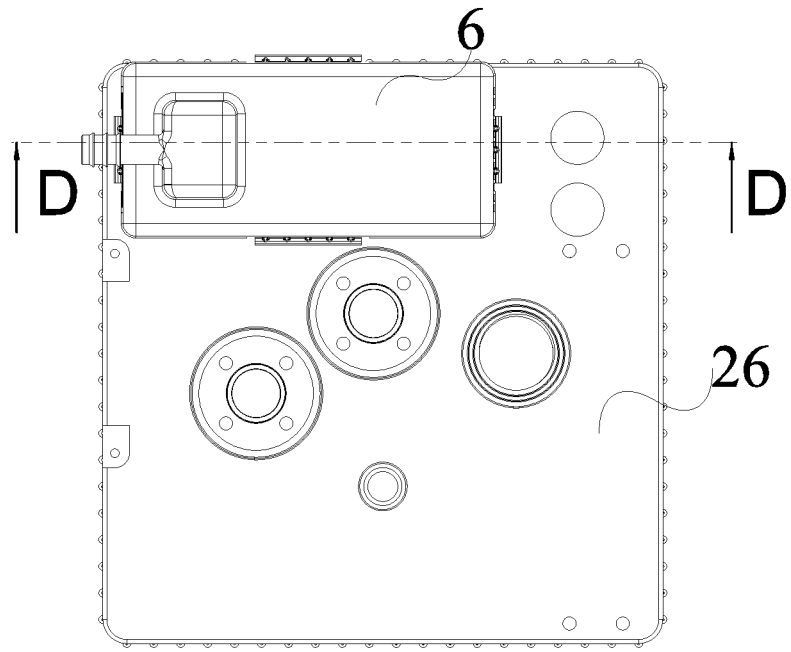
FIG. 20A and FIG. 20B show a top view diagram and a cross-section diagram crossing along the D-D line of the top view diagram of the present invention which only has the condense filter and the cover body of the water tank in the embodiment shown in FIG. 18A.
Figure 20B:
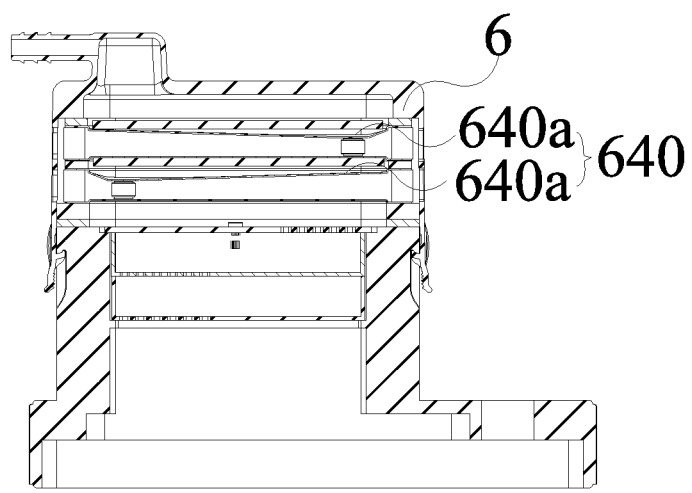

Please refer to FIG. 18A, FIG. 18B, FIG. 19, FIG. 20A, and FIG. 20B. FIG. 18A and FIG. 18B show a schematic diagram of the gas generator in the fifteenth embodiment with different visual angles of the present invention, FIG. 19 shows a back view diagram of the gas generator in the embodiment shown in FIG. 18A of the present invention, and FIG. 20A and FIG. 20B show a top view diagram and a cross-section diagram crossing along the D-D line of the top view diagram of the present invention which only has the condense filter and the cover body of the water tank in the embodiment shown in FIG. 18A. In the fifteenth embodiment, the gas generator of the present invention comprises a water tank electrolysis device, a nebulized gas mixing tank, a water pump, a condense filter, a cooling device, and a humidification device. The structure of the elements mentioned above has been explained in the above statement, so unnecessary details will not be given again herein. Additionally, compared with the circulating channel shown in FIG. 14B, in this embodiment shown in FIG. 20B, the circulating channel 640 can achieve the goal of condensing when the circulating channel is formed by two channel 640a only, which will simplify the design and reduce the cost of the condense filter 6 as well. Furthermore, in this embodiment, the water pump 5 (not shown in the figure), the condense filter 6, and the cooling device 7 are integrated and then disposed on the cover body of the water tank 2. Compared with the fourteenth embodiment, the design mentioned above can save much more space. Additionally, when the water tank 2, the water pump 5, the condense filter 6, and the cooling device 7 are assembled with the nebulized gas mixing tank 4 and the humidification device 9, the present invention has the advantages of convenient assembling and simplified piping for optimizing the design of the gas generator of the present invention.

To summarize the statement mentioned above, the present invention provides a gas generator, a comprising electrolysis device, a cooling device, and a water pump. The gas generator of the present invention can utilize the cooling device to cool down the electrolyzed water after the hydrogen-oxygen mixed gas is generated, and utilize the water pump to enforce to circulate the electrolyzed water to achieve the goal of heat radiation. Meanwhile, the present invention can allow the temperature of the electrolyzed water to be in a temperature range of providing optimal electrolytic efficiency for effectively electrolyzing electrolyzed water to generate hydrogen-oxygen mixed gas, to solve the energy consumption problems. Furthermore, the gas generator of the present invention utilizes the design of disposing the electrolysis device in the water tank to save space. Meanwhile, through the first hollow portion of the water tank is full of hydrogen-oxygen mixed gas generated by the electrolysis device and the electrolyzed water in the electrolysis device, the gas chamber in the water tank can be eliminated and the temperature of the electrolysis device can be decreased to reduce the possibility of gas explosions. Additionally, the design of the gas outlet and the inlet opening of the electrolysis device of the present invention allows the electrolyzed water in the water tank to be recharged in the electrolysis device, and the hydrogen-oxygen mixed gas generated by the electrolysis device can be outputted from the water tank to achieve the goal of water-gas circulation. Furthermore, the water pump, the water tank, and the electrolysis device of the present invention are connected with each other, which can enforce to circulate the electrolyzed water in the first hollow portion and the electrolysis device for eliminating gas chambers so as to reduce the possibility of gas explosions. Additionally, the hydrogen-oxygen mixed gas generated by the electrolysis device can be cooled down and filtered by the condense filter, to provide a hydrogen-oxygen mixed gas which is appropriate for humans to breathe. Meanwhile, through the design of the present invention, the electrolyte can be flushed back to the electrolysis device while recharging water, used to decrease the consumption of the electrolyte and avoid the electrolyte to block the condense filter. Furthermore, the hydrogen-oxygen mixed gas generated by the electrolysis device can be humidified by the humidification device, to provide a hydrogen-oxygen mixed gas which is appropriate for humans to breathe. Additionally, through the humidification device, the hydrogen-oxygen mixed gas generated by the electrolysis device can generate hydrogen water with higher concentration of hydrogen-oxygen mixed gas. In practical application, the concentration of hydrogen-oxygen mixed gas of the hydrogen water can be adjusted according to the requirement of the user. And the design of the present invention can be used to recharge recharged water. Meanwhile, the electrolyte will be flushed back to the electrolysis device to recover the filter ability of the circulating channel, avoid the circulating channel to be blocked or corroded, and decrease the consumption of the electrolyte.

Figure 21A:
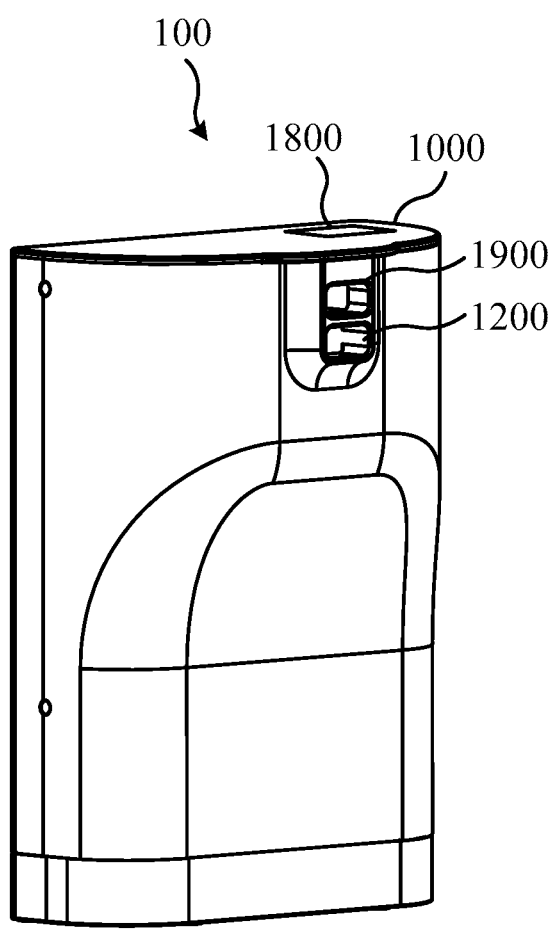
FIG. 21A shows a schematic diagram of the hydrogen water generator in an embodiment of the present invention.
Figure 21B:
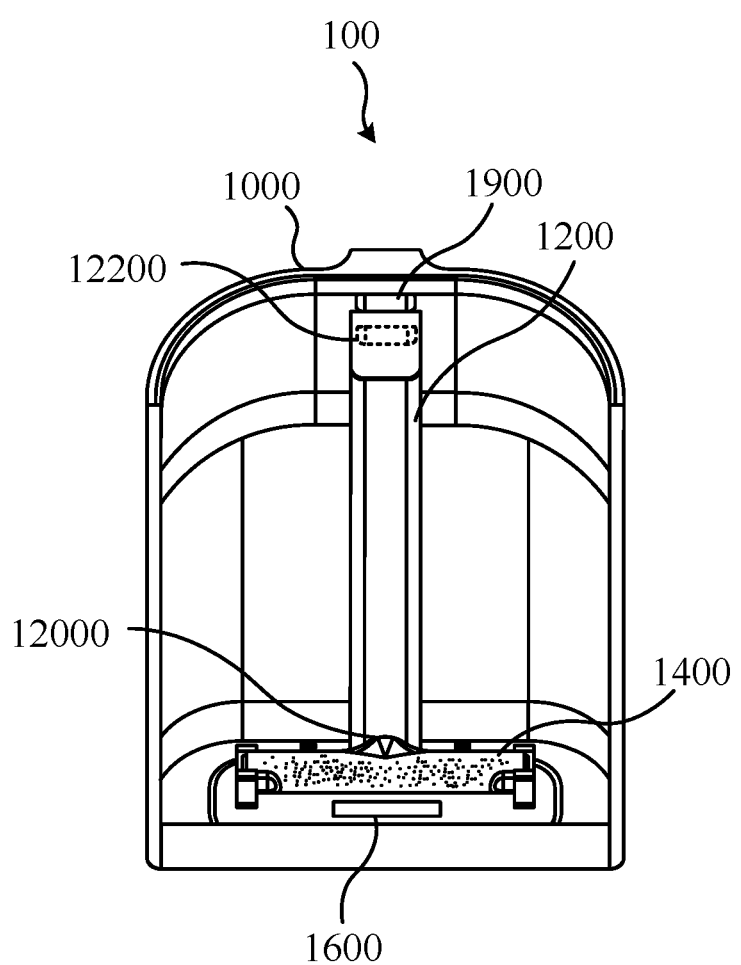
FIG. 21B shows a schematic diagram of the interior of the hydrogen water generator shown in FIG. 21A in an embodiment of the present invention.

Please refer to FIG. 21A and FIG. 21B. FIG. 21A shows a schematic diagram of the hydrogen water generator in an embodiment of the present invention, and FIG. 21B shows a schematic diagram of the interior of the hydrogen water generator shown in FIG. 21A in an embodiment of the present invention. It is worth noting that the visual angle in FIG. 21A is different from the visual angel in FIG. 21B, which is used for showing the interior of the hydrogen water generator clearly. The hydrogen water generator 100 comprises a container 1000, a gas inlet pipe 1200, a thinning pipe 1400, an oscillation device 1600, and a liquid inputting/outputting structure 1800. The container 1000 can be used to contain water. But in the practical application, the container 1000 is not limited to contain water, and the container 1000 also can be used to contain liquid according to the requirement. The gas inlet pipe 1200 is disposed on the container 1000, comprising a first end 12000 extending to the interior of the container 1000, and a second end 12200 connecting to the outside part of the container 1000. Therefore, the gas inlet pipe 1200 can receive gas comprising hydrogen from a hydrogen source through the second end 12200, and then input the gas comprising hydrogen into the container 1000, wherein the gas comprising hydrogen can be pure hydrogen or hydrogen-oxygen mixed gas in practical application.

The first end 12000 of the gas inlet pipe 1200 mentioned above is connected to the middle of the thinning pipe 1400. The received gas comprising hydrogen can be inputted into the thinning pipe 1400. The surface of the thinning pipe 1400 has vias for the gas comprising hydrogen to pass through to the interior of the container 1000. Additionally, the two ends of the thinning pipe 1400 is closed, to prevent the leakage of the gas comprising hydrogen or avoid the water contained in the container 1000 to get into the thinning pipe 1400.

In this embodiment, the vias is used for allowing the gas comprising hydrogen to be formed as a plurality of thin bubbles after outputting from the thinning pipe 1400 to the water contained in the container 1000 through the vias. In practical application, the scale of the via is between 2 meters and 10 meters. But the present invention is not limited to the statement mentioned above. The scale can be adjusted according to the requirement.

Additionally, the hydrogen water generator 1000 further comprises an oscillation device 1600, used to further increase the solubility of hydrogen. The oscillation device 1600 is disposed in the container 1000, used to oscillate the water contained in the container 1000. As shown in the FIG. 21B, in this embodiment, the oscillation device 1600 is disposed on the bottom of the container 1000. The oscillation device 1600 can comprise an ultrasonic wave oscillation device for oscillating the water in the container 1000, for allowing the hydrogen to be effectively distributed in the water, which allows the concentration of the hydrogen to be increased to form hydrogen water. Furthermore, the oscillation device can comprise a centrifugal blade and a driving motor connected to the centrifugal blade. The driving motor can drive the centrifugal blade to rotate for generating swirl in the water to help hydrogen to be effectively distributed in the water to form hydrogen water.

Please refer to FIG. 21A, the hydrogen water generator 100 further comprises a liquid inputting/outputting structure 1800. The liquid inputting/outputting structure 1800 shown in FIG. 21A is a liquid inputting/outputting opening. Through the liquid inputting/outputting opening 1800, the container 1000 can be recharged with water from the exterior, and the hydrogen water also can be outputted from the container 1000. In practical application, the liquid inputting/outputting structure also can be a straw-shaped device connected between the exterior and the interior of the container. Furthermore, the liquid inputting/outputting structure also can be designed as an inlet structure and an outlet structure, such as an inlet opening and an outlet opening, to provide the same function mentioned above.

In the embodiment shown in FIG. 21A, the hydrogen water generator 100 further comprises a gas outlet structure 1900. When the humidified gas comprising hydrogen floats up to the container 1000, the humidified gas comprising hydrogen can be collected by the gas outlet structure 1900 and then be outputted to the exterior. In practical application, the generated flow rate of the humidified gas outputted from the gas outlet structure 1900 can be between 0.01 L/min to 12 L/min.

To summarize the statement mentioned above, the hydrogen water generator can generate hydrogen water and humidified gas easily. The generated hydrogen water will not comprise excess minerals or magnesia, so the filter process is not required.

Figure 22:
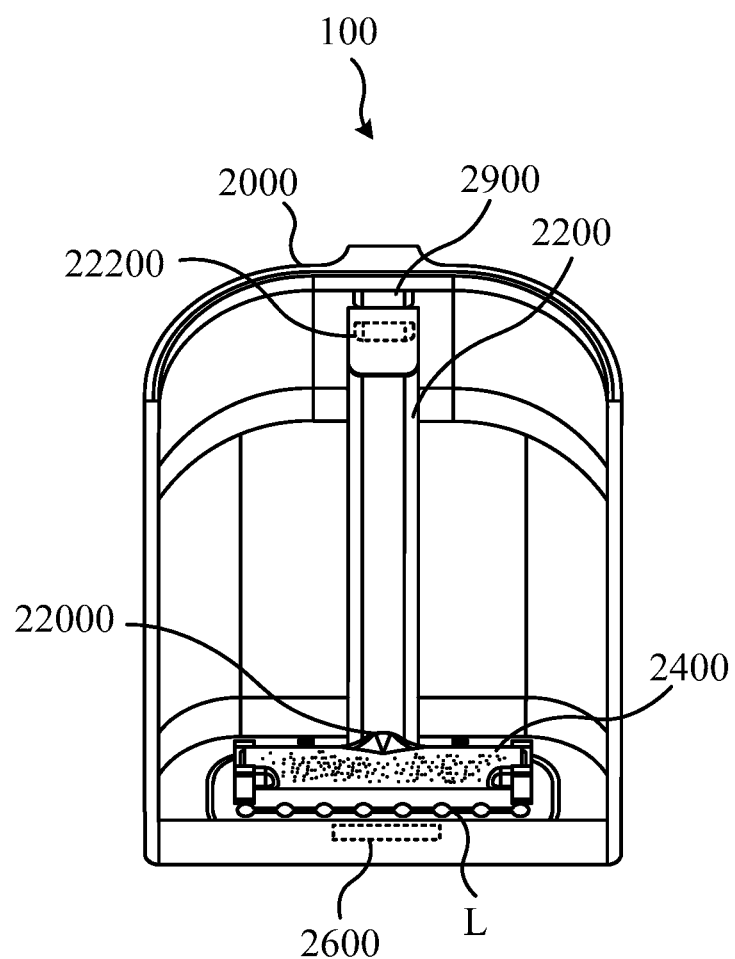
FIG. 22 shows a schematic diagram of the hydrogen water generator in another embodiment of the present invention.

Please refer to FIG. 22. FIG. 22 shows a schematic diagram of the hydrogen water generator in another embodiment of the present invention. In this embodiment, the container 2000 of the hydrogen water generator 500 has a transparent side wall. A User can observe the interior of the container 2000 through the transparent side wall. Additionally, the hydrogen water generator 500 in this embodiment further has a light emitting device L, used to emit light to the interior of the container 2000, and the light will be emitted from the container 2000 to outside through the transparent side wall of the container 2000.

In this embodiment, the light emitting device L is a LED light emitting device, which can be used to emit different color of light. In practical application, the light emitting device L is not limited to the LED light emitting device. Any device which can achieve the function mentioned above is comprised in the present invention. Additionally, the light emitting device L is not limited to be disposed on the bottom of the container 2000. For example, the LED light emitting device also can be disposed on the non-transparent side wall of the container 2000 to achieve different visual effects.

Therefore, the hydrogen water generator can not only generate hydrogen water and humidified gas easily and effectively, but also provide some visual effects through the light emitting device.

Additionally, in the embodiment shown in FIG. 1B, the first end 12000 of the gas inlet pipe 1200 is connected to the middle of the thinning pipe 1400. But in practical application, the connection type can be different. According to another embodiment of the present invention, the middle part of the thinning pipe of the hydrogen water generator does not have an opening to be connected with the gas outlet pipe. The thinning pipe uses one end to connect with the first end of the gas inlet pipe. The surface of the thinning pipe also has vias and the other end of the thinning pipe is closed.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator, comprising:
a water tank having a first hollow portion for containing electrolyzed water; and
an electrolysis device electrolyzing the electrolyzed water to generate a gas comprising hydrogen, wherein the electrolysis device comprises an electrolysis housing, a plurality of electrodes disposed in an inner space of the electrolysis housing, and a partition formed by extending outward from the outside surface of the electrolysis housing, the electrolysis housing is disposed inside the first hollow portion of the water tank, the partition divides the first hollow portion into an upper portion and a lower portion, and the upper portion and the lower portion are fluidly coupled to the inner space of the electrolysis device respectively.

2. The gas generator of claim 1, further comprising:
a cooling device configured to cool down the electrolyzed water from the water tank;
a water pump configured to circulate the electrolyzed water from the upper portion of the water tank to the cooling device and then to the lower portion of the water tank.

3. The gas generator of claim 2, further comprising a microcomputer controller, the microcomputer controller coupled to the water pump and configured to detect the temperature of the electrolyzed water and control a flow rate of the water pump according to the detected temperature of the electrolyzed water.

4. The gas generator of claim 3, wherein the microcomputer controller comprises a temperature sensor, and the temperature sensor is used to detect the temperature of the electrolyzed water.

5. The gas generator of claim 1, further comprising a humidification device coupled to the electrolysis device to humidify the gas comprising hydrogen.

6. The gas generator of claim 1, wherein a bottom of the electrolysis device has a plurality of lower vias fluidly coupled to the lower portion of the water tank.

7. The gas generator of claim 1, wherein the electrolysis device comprises a pad disposed above a surface of each electrode, wherein the pad has a plurality of upper vias to output the gas comprising hydrogen to the water tank.

8. The gas generator of claim 7, wherein an electrode channel is formed between two adjacent electrodes such that a set of electrode channels are formed within the plurality of electrodes, and the set of electrode channels are corresponding to the plurality of upper vias.

9. The gas generator of claim 7, wherein the electrolysis device comprises a plurality of protrusions formed by extending inward from the side surface of the electrolysis housing, and the plurality of protrusions are configured to fix the plurality of electrodes in the inner space of the electrolysis housing.

10. The gas generator of claim 1, wherein the water tank further comprises a pipe for outputting the gas comprising hydrogen and refilling the electrolyzed water into the first hollow portion of the water tank.

11. A gas generator, comprising:
an electrolysis device electrolyzing electrolyzed water to generate a gas comprising hydrogen, wherein the electrolyzed water contains an electrolyte;
a condense filter coupled to the electrolysis device to filter the electrolyte out of the gas comprising hydrogen to form a filtered gas comprising hydrogen; and
a humidification device configured to contain a supplemental water for humidifying the filtered gas comprising hydrogen to form a humidified gas comprising hydrogen;
wherein the condense filter is capable to receive the supplemental water from the humidification device to flush the electrolyte out of the condense filter.

12. The gas generator of claim 11, wherein the condense filter has a gas inlet via and a gas outlet via, the gas inlet via is coupled to the electrolysis device for receiving the gas comprising hydrogen, and the gas outlet via is configured to output the filtered gas comprising hydrogen; wherein the gas outlet via of the condense filter is capable to receive the supplemental water to flush the electrolyte back to the electrolysis device through the gas inlet via.

13. The gas generator of claim 12, wherein the condense filter comprises a plurality of condense plates, each condense plate has a space to form a channel, and the channel of the condense plate is coupled with the adjacent channel of the condense plate for the gas comprising hydrogen to flow through, and the channel of the condense plate is positioned between the gas inlet via and the gas outlet via.

14. The gas generator of claim 11, further comprising a water tank having a first hollow portion for containing the electrolyzed water, wherein the electrolysis device having an electrolysis housing is disposed inside the first hollow portion of the water tank.

15. The gas generator of claim 14, wherein the condense filter is capable to receive the supplemental water to flush the electrolyte back to the water tank.

16. The gas generator of claim 11, wherein the humidification device comprises a container with a hollow space, a second pipe, and a outputting pipe, the container contains the supplemental water, the second pipe is coupled to the container for receiving the filtered gas comprising hydrogen, the outputting pipe is coupled to the second pipe, the surface of the outputting pipe has a plurality of vias for outputting the filtered gas comprising hydrogen into the supplemental water.

17. The gas generator of claim 11, further comprising a nebulized gas mixing tank to mix a nebulized medicine generated by the nebulized gas mixing tank with the humidified gas comprising hydrogen.

18. The gas generator of claim 11, wherein the condense filter is capable to receive the supplemental water to flush the electrolyte back to the electrolysis device.

* * * * *